United States Patent [19]
Tyagi et al.

[11] Patent Number: 6,103,476
[45] Date of Patent: *Aug. 15, 2000

[54] DETECTABLY LABELED, DUAL CONFORMATION OLIGONUCLEOTIDE PROBES, ASSAYS AND KITS

[75] Inventors: Sanjay Tyagi, New York; Fred R. Kramer, Riverdale, both of N.Y.; Paul M. Lizardi, Cuernavaca, Mexico

[73] Assignee: The Public Health Research Institute of the City of New York, Inc., N.Y.

[*] Notice: This patent is subject to a terminal disclaimer.

[21] Appl. No.: 09/268,402

[22] Filed: Mar. 15, 1999

Related U.S. Application Data

[63] Continuation of application No. 08/439,819, May 12, 1995, Pat. No. 5,925,517, which is a continuation-in-part of application No. 08/152,006, Nov. 12, 1993, abandoned.

[51] Int. Cl.$^7$ .............................. C12Q 1/68; C12P 19/34
[52] U.S. Cl. .............................................. 435/6; 435/91.2
[58] Field of Search ..................... 435/6, 91.2; 536/24.2, 536/25.32

[56] References Cited

U.S. PATENT DOCUMENTS

| | | | |
|---|---|---|---|
| 4,261,968 | 4/1981 | Ullman et al. | 424/8 |
| 4,725,536 | 2/1988 | Fritsch et al. | 435/6 |
| 4,725,537 | 2/1988 | Fritsch et al. | 435/6 |
| 4,752,566 | 6/1988 | Collins et al. | 435/6 |
| 4,766,062 | 8/1988 | Diamond et al. | 435/6 |
| 4,822,733 | 4/1989 | Morrison | 435/6 |
| 4,996,143 | 2/1991 | Heller et al. | 436/6 |
| 5,082,830 | 1/1992 | Brakel et al. | 514/44 |
| 5,118,801 | 6/1992 | Lizardi et al. | 436/6 |
| 5,210,015 | 5/1993 | Gelfand et al. | 435/6 |
| 5,241,060 | 8/1993 | Engelhardt et al. | 536/27 |
| 5,260,433 | 11/1993 | Engelhardt et al. | 536/23 |
| 5,312,921 | 5/1994 | Glazer et al. | 546/108 |
| 5,332,659 | 7/1994 | Kidwell | 435/6 |
| 5,348,853 | 9/1994 | Wang et al. | 435/6 |
| 5,487,972 | 1/1996 | Gelfand et al. | 435/6 |
| 5,491,063 | 2/1996 | Fisher et al. | 435/6 |
| 5,527,676 | 6/1996 | Vogelstein et al. | 435/6 |
| 5,532,129 | 7/1996 | Heller et al. | 435/6 |
| 5,538,848 | 7/1996 | Livak et al. | 435/5 |
| 5,565,322 | 10/1996 | Heller | 435/6 |
| 5,571,673 | 11/1996 | Picone | 435/6 |
| 5,622,821 | 4/1997 | Selvin et al. | 435/6 |

FOREIGN PATENT DOCUMENTS

| | | |
|---|---|---|
| B-57754/86 | 11/1986 | Australia. |
| 0 070 685 A2 | 1/1983 | European Pat. Off.. |
| 0 232 967 A2 | 8/1987 | European Pat. Off.. |
| 0 286 898 A3 | 10/1988 | European Pat. Off.. |
| 0 364 255 A2 | 4/1990 | European Pat. Off.. |
| 0 601 889 A2 | 6/1994 | European Pat. Off.. |
| 0 640 828 A1 | 3/1995 | European Pat. Off.. |
| 0 745 690 A2 | 12/1996 | European Pat. Off.. |
| 5-123195 | 5/1993 | Japan. |
| 92/14845 | 9/1992 | WIPO. |
| WO 95/13399 | 5/1995 | WIPO. |

OTHER PUBLICATIONS

B.C. Bagwell, et al., "A New Homogenous Assay System For Specific Nucleic Acid Sequences: Poly–dA And Poly–A Detection," Nucleic Acids Research 22: 2424–2425 (1994).
J. Brand, et al., "Fluorescence Probes For Structure," Ann Rev Biochemistry 41: 843–868 (1972).
K.J. Breslauer, et al., "Predicting DNA Duplex Stability From The Base Sequence," P.N.A.S. (U.S.A.) 83: 3746–3750 (1986).
C.R. Cantor, et al., "Techniques For The Study Of Biological Structure And Function," (W.H. Freeman and Co., San Francisco) (U.S.A) pp. 448–455 (1980).
C.R. Cantor, "Lighting Up Hybridization," Nature Biotechnology 14: 264 (1996).
Cardullo, et al., "Detection Of Nucleic Acid Hybridization By Nonradiative Fluorescence Resonance Energy Transfer," P.N.A.S. (U.S.A.) 85: 8790–8794 (1988).
A. Coghlan, "Brilliant Beacons Colour–Code Genes," New Scientist p. 24 (Mar. 16, 1996).
B.A. Connolly, et al., "Chemical Synthesis Of Oligonucleotides Containing A Free Sulphydryl Group And Subsequent Attachment Of Thiol Probes," Nucleic Acids Research 13: 4485–4502, 1985.
J.P. Cooper, et al., "Analysis Of Fluorescence Energy Transfer In Duplex And Branched DNA Molecules," Biochemistry 29: 9261–9268 (1990).
M.E. DePecol, et al., "Sytheses, Properties, And Use Of Fluorescent N–(5'–Phospho–4'–Pyridoxyl) Amines In Assay Of Pyridoxamine (Pyridoxine) 5'–Phosphate Oxidase," Analytical Biochemistry 101: 435–441 (1980).
H.A. Erlich, et al., "Recent Advances In The Polymerase Chain Reaction," Science 252: 1643–1651 (1991).
D. Gillespie, et al., "A Quantitative Assay For DNA–RNA Hybrids With DNA Immobilized On A Membrane," J. Mol. Biol. 12: 829–842 (1965).
Z. Guo, et al., "Enhanced Discrimination Of Single Nucleotide Polymorphisms By Artificial Mismatch Hybridization," Nature Biotechnology 15: 331–335 (1997).
R.P. Haugland, et al., "Dependence Of The Kinetics Of Singlet–Singlet Energy Transfer On Spectral Overlap," P.N.A.S. (U.S.A.) 63: 23–30 (1969).

(List continued on next page.)

*Primary Examiner*—Eggerton A. Campbell
*Attorney, Agent, or Firm*—Fish & Richardson P.C.

[57] ABSTRACT

Unimolecular and bimolecular hybridization probes for the detection of nucleic acid target sequences comprise a target complement sequence, an affinity pair holding the probe in a closed conformation in the absence of target sequence, and either a label pair that interacts when the probe is in the closed conformation or, for certain unimolecular probes, a non-interactive label. Hybridization of the target and target complement sequences shifts the probe to an open conformation. The shift is detectable due to reduced interaction of the label pair or by detecting a signal from a non-interactive label. Certain unimolecular probes can discriminate between target and non-target sequences differing by as little as one nucleotide. Also, universal stems and kits useful for constructing said probes. Also, assays utilizing said probes and kits for performing such assays.

12 Claims, 14 Drawing Sheets

OTHER PUBLICATIONS

P.M. Holland, et al., "Detection Of Specific Polymerase Chain Reaction Product By Utilizing the 5'–3' Exonuclease Activity Of Thermus Aquaticus DNA Polymerase," P.N.A.S. (U.S.A.) 88: 7276–7280 (1991).

P.M. Holland, et al., "Detection Of Specific Polymerase Chain Reaction Product By Utilizing the 5'–3' Exonuclease Activity Of Thermus Aquaticus DNA Polymerase," Clinical Chemistry 38: 462–463 (1992).

E.N. Hudson, et al., "Synthesis And Characterization Of Two Fluorescent Sulfhydryl Reagents," Biochemistry 12: 4154–4161 (1973).

V.M. Ingram, "Gene Mutations In Human Haemoglobin: The Chemical Difference Between Normal And Sickle Cell Haemoglobin," Nature 180: 326–328 (1957).

U. Landegren, et al., "A Ligase–Mediated Gene Detection Technique," Science 241: 1077–1080 (1988).

R. Lathe, "Synthetic Oligonucleotide Probes Deduced From Amino Acid Sequence Data, Theoretical And Practical Considerations," J. Mol. Biol. 183: 1–12 (1985).

L.G. Lee, et al., "Allelic Discrimination By Nick–Translation PCR With Fluorogenic Probes," Nucleic Acid Research 21: 3761–3766 (1993).

P. Lichter, et al., "High–Resolution Mapping Of Human Chromosome 11 By In Situ Hybridization With Cosmid Clones," Science 247: 64–69 (1990).

K.J. Livak, et al., "Towards Fully Automated Genome–Wide Polymorphism Screening," Nature Genetics 9: 341–342 (1995).

H. Lomell, et al., "Quantitative Assays Based On The Use Of Replicatable Hybridization Probes," Clinical Chemistry 35: 1826–1831 (1989).

E.D. Matayoshi, et al., "Novel Fluorogenic Substrates For Assaying Retroviral Proteases By Resonance Energy Transfer," Science 247: 954–958 (1990).

J.A. Matthews, et al., "Analytical Strategies For The Use Of DNA Probes," Analytical Biochemistry 169: 1–25 (1988).

L.E. Morrison, et al., "Sensitive Fluorescence–Based Thermodynamic And Kinetic Measurements Of DNA Hybridization In Solution," Biochemistry 32: 3095–3104 (1993).

L.E. Morrison, et al., "Solution–Phase Detection Of Polynucleotides Using Interacting Fluorescent Labels And Competitive Hybridization," Analytical Biochemistry 183: 231–244 (1989).

N.C. Nelson, et al., "Detection Of All Single–Base Mismatches In Solution By Chemiluminescence," Nucleic Acid Research 24: 4998–5003 (1996).

P.S. Nelson, et al., "Bifunctional Oligonucleotide Probes Synthesized Using A Novel CPG Support Are Able To Detect Single Base Pair Mutations," Nucleic Acids Research 17: 7187–7194 (1989).

Newton, et al., Analysis Of Any Point Mutation In DNA. The Amplification Refractory Mutation System (ARMS) Nucleic Acids Research 17: 2503–2516 (1989).

M. Orita, et al., "Detection Of Polymorphisms Of Human DNA By Gel Electrophoresis As Single–Strand Conformation Polymorphism" P.N.A.S. (U.S.A.) 86: 2766–2770 (1989).

H. Orum, et al., "Single Base Pair Mutation Analysis By PNA Directed PCR Clamping," Nucleic Acids Research 21: 5332–5336 (1993).

K.M. Parkhurst, et al., "Kinetic Studies Of Oligonucleotide–DNA Hybridization In Solution By Fluorescence . . . ," 37th Ann. Meeting of the Biophysical Society, Washington, D.C., Abstract W–Pos97, 1993.

R.K. Saiki, et al., "Genetic Analysis Of Amplified DNA With Immobilized Sequence–Specific Oligonucleotide Probes," P.N.A.S. (U.S.A.) 86: 6230–6234 (1989).

Sambrook, et al., "Molecular Cloning: A Laboratory Manual," Synthetic Oligonucleotide Probes, 1989, Cold Spring Harbor Lab Press pp. 11.47 and 11.55–11.57.

P.R. Selvin, "Fluorescence Resonance Energy Transfer," Methods in Enzymology 246: 300–335 (1995).

D. Shore, et al., "DNA Flexibility Studied By Covalent Closure Of Short Fragments Into Circles," P.N.A.S. (U.S.A.) 78: 4833–4837 (1981).

S. Sixou, et al., "Intracellular Oligonucleotide Hybridization Detected By Fluorescence Resonance Energy Transfer (FRET)," 37th Ann. Meeting of the Biophysical Society, Washington, D.C., Abstract Tu–Pos351, 1993.

S. Sixou, et al., "Intracellular Oligonucleotide Hybridization Detected By Fluorescence Resonance Energy Transfer," Nucleic Acids Research 22: 662–668 (1994).

L. Stryer, "Fluorescence Energy Transfer As A Spectroscopic Ruler," Ann. Rev. Biochem. 47: 819–846 (1978).

N. Tibanyenda, et al., The Effect Of Single Base–Pair Mismatches On The Duplex Stability Of d(T–A–T–T–A–A–T –A–T–C–A–A–G–T–T–G) • d(C–A–A–C–T–T–G–A–T–A–T–T–A–A–T–A), Eur. J. Biochem. 139: 19–27 (1984).

S. Tyagi, et al., Molecular Beacons: Probes That Fluoresce Upon Hybridization, Nature Biotechnology 14: 303–308 (1996).

E.F. Ullman, et al., "Fluorescent Excitation Transfer Immunoassay," The Journal of Biological Chemistry 251: 4172–4178 (1976).

G.T. Walker, et al., Strand Displacement Amplification—An Isothermal, In Vitro DNA Amplification Technique Nucleic Acids Research 20: 1691–1696 (1992).

G.T. Wang, et al., "Design And Synthesis Of New Fluorogenic HIV Protease Substrates Based On Resonanc Energy Transfer," Tetrahedron Letters 31: 6493–6496 (1990).

H. Werntges, et al., "Mismatches In DNA Double Strands: Thermodynamic Parameters And Their Correlation To Repair Efficiencies," Nucleic Acids Research 14: 3773–3790 (1986).

S.J. Wood, "DNA–DNA Hybridization In Real Time Using BIAcore," Microchemical Journal 47: 330–337 (1993).

C. Yang et al., "Studies Of Transfer RNA Tertiary Structure By Singlet–Singlet Energy Transfer," P.N.A.S. (U.S.A.) 71: 2838–2842 (1974).

R. Youil et al., "Screening For Mutations By Enzyme Mismatch Cleavage With T4 Endonuclease," VII.P.N.A.S (U.S.A.) 92: 87–91 (1995).

Guatelli et al., "Isothermal in vitro amplification of nucleic acids by a multienzyme reaction modeled after retroviral replication," Proc. Natl. Acad. Sci. USA 87:1874–1878, 1990.

Landegren, U., "Molecular mechanics of nucleic acid sequence amplification," Trends Genet. 9:199–204, 1993.

Muesing et al., "Nucleic acid structure and expression of the human AIDS/adenopathy retrovirus," Nature 313:450–458, 1985.

Stryer, L., "Fluorescence Spectroscopy of Proteins," Science 162:526–533, 1968.

Michael et al., "The Role of CCR5 and CCR2 Polymorphisms in HIV–1 Transmission and Disease Progression," Nature Medicine 3:1160–1162, and related editorial on p. 1051, 1997.

Smith et al., "Contrasting Genetic Influence of CCR2 and CCR5 Variants on HIV–1 Infection and Disease Progression," Science 277:959–965, 1997.

DETECTABLY LABELED, DUAL CONFORMATION OLIGONUCLEOTIDE PROBES, ASSAYS AND KITS

This application is a continuation of application Ser. No. 08/439,819, filed May 12, 1995, now U.S. Pat. No. 5,925,517, which is a continuation-in-part of application Ser. No. 08/152,006, filed Nov. 12, 1993, now abandoned.

The present invention relates to the field of assays which involve nucleic acid hybridization probes. Assays are useful for the detection of specific genes, gene segments, RNA molecules and other nucleic acids. Such assays are used clinically, for e.g., tissue, blood and urine samples, as well as in food technology, agriculture and biological research.

BACKGROUND OF THE INVENTION

Nucleic acid hybridization probes are used to detect specific target sequences in a complex mixture. Conventional, heterogeneous, hybridization assays, such as those described in Gillespie and Spiegelman (1965), typically comprise the following steps: immobilization of at least the target nucleic acid on paper, beads, or plastic surfaces, with or without using capture probes; addition of an excess of labelled probes that are complementary to the sequence of the target; hybridization; removal of unhybridized probes; and detection of the probes remaining bound to the immobilized target.

Unhybridized probes are removed by extensive washing of the hybrids. This is generally the most time-consuming part of the procedure, and often utilizes complex formats such as sandwich hybridization. The use of solid surfaces lengthens the time it takes for hybridization by restricting the mobility of, or access to, the target. The large area presented by the solid surfaces nonspecifically retains unhybridized probes, leading to background signal. Additionally, solid surfaces may interfere with signal from the probes. The requirement that the probe-target hybrids be isolated precludes in vivo detection and concurrent detection of nucleic acids during synthesis reactions (real-time detection).

Several solution-phase detection schemes, sometimes referred to as homogeneous assays, are known. By "homogeneous" we mean assays that are performed without separating unhybridized probes from probe-target hybrids. These schemes often utilize the fact that the fluorescence of many fluorescent labels can be affected by the immediate chemical environment. One such scheme is described by Heller et al. (1983) and also by Cardullo et al. (1988). It uses a pair of oligodeoxynucleotide probes complementary to contiguous regions of a target DNA strand. One probe contains a fluorescent label on its 5' end and the other probe contains a different fluorescent label on its 3' end. When the probes are hybridized to the target sequence, the two labels are very close to each other. When the sample is stimulated by light of an appropriate frequency, fluorescence resonance energy transfer ("FRET") from one label to the other occurs. This energy transfer produces a measurable change in spectral response, indirectly signaling the presence of target. The labels are sometimes referred to as FRET pairs. However, the altered spectral properties are subtle, and the changes are small relative to background signal. Monitoring requires sophisticated instruments, and, even so, sensitivity is limited. Moreover, the hybridization signal is, in some cases, a negative one; i.e., the presence of target results in a reduction in the amount of fluorescence measured at a particular wavelength.

This technique requires that two unassociated probes bind simultaneously to a single-stranded target sequence. The kinetics of this tri-molecular hybridization are too slow for this technique to be suitable for real-time detection. The requirement that target be single-stranded makes the technique unsuitable for in vivo detection of double-stranded nucleic acids.

Another solution-phase scheme also utilizes a pair of oligodeoxynucleotide probes. However, here the two probes are completely complementary both to each other and to complementary strands of a target DNA (Morrison, 1987; Morrison, 1989; Morrison et al., 1989; Morrison and Stols, 1993). Each probe includes a fluorophore conjugated to its 3' end and a quenching moiety conjugated to its 5' end.

When the two oligonucleotide probes are annealed to each other, the fluorophore of each probe is held in close proximity to the quenching moiety of the other probe. If the fluorescent label is then stimulated by an appropriate frequency of light, the fluorescence is quenched by the quenching moiety. However, when either probe is bound to a target, the quenching effect of the complementary probe is absent. The probes are sufficiently long that they do not self-quench when target-bound.

In this type of assay, there are two opposing design considerations. It is desirable to have a high concentration of probes to assure that hybridization of probes to target is rapid. It is also desirable to have a low concentration of probes so that the signal from probes bound to target is not overwhelmed by background signal from probes not hybridized either to target or other probes. This situation necessitates waiting a relatively long time for the background fluorescence to subside before reading the fluorescent signal.

An assay according to this scheme begins by melting a mixture of probes and sample that may contain target sequences. The temperature is then lowered, leading to competitive hybridization. Some probes will hybridize to target, if present; some will hybridize to complementary probes; and some will not hybridize and create background signal. A parallel control assay is run with no target, giving only a background level of fluorescence. If the sample contains sufficient target, a detectably higher level of residual fluorescence is obtained.

With this scheme it is necessary to delay reading the residual fluorescence for a considerable time to permit nearly all the excess probes to anneal to their complements. Also, a parallel control reaction must be performed. Additionally, a low concentration of probes is used to reduce the fluorescent background. Thus, kinetics are poor and result in an inherently slow assay. That precludes real-time detection. These problems are particularly severe for double-stranded targets. The probes, as well as the targets, need to be melted, rendering the assay unsuitable for use in vivo. Also, the signal is not only residual, it is a differential signal from comparison to an external control.

Another solution-phase scheme utilizing the phenomenon known as strand displacement is described by Diamond et al., 1988. Typically, these assays involve a bimolecular nucleic acid probe complex. A shorter single-strand comprising a subset of the target sequence is annealed to a longer probe single-strand which comprises the entire target binding region of the probe. The probe complex reported thus comprises both single-stranded and double-stranded portions. The reference proposed that these probe complexes may further comprise either a $^{32}P$ label attached to the shorter strand or a fluorophore and a quencher moiety which could be held in proximity to each other when the probe complex is formed.

It is stated that in assays utilizing these probe complexes, target detection is accomplished by a two-step process. First, the single-stranded portion of the complex hybridizes with the target. It is described that target recognition follows thereafter when, through the mechanism of branch migration, the target nucleic acid displaces the shorter label-bearing strand from the probe complex. The label-bearing strand is said to be released into solution, from which it may be isolated and detected. In an alternative arrangement reported as a $^{32}$P labeled probe for a capture procedure, the two single-stranded nucleic acids are linked together into a single molecule.

These strand-displacement probe complexes have drawbacks. The mechanism is two-step, in that the probe complex must first bind to the target and then strand-displacement, via branch migration, must occur before a target is recognized and a signal is generated. Bimolecular probe complexes are not reported to form with high efficiency, resulting in probe preparations wherein the majority of the target binding regions may not be annealed to a labeled strand. This may lead to competition between label-bearing and label-free target binding regions for the same target sequence. Additionally, there may be problems with non-specific fall-off of labeled strands. Moreover, the displaced labeled strand may need to be separated from the unhybridized probe complexes before a signal may be detected. This requirement would make such a probe complex unsuitable for a homogeneous assay.

A drawback of prior art homogeneous and heterogeneous assays employing labeled probes is the difficulty in achieving hybridization to a preselected target sequence while avoiding hybridization to other sequences differing slightly from the target sequence. The permissible range of conditions tends to be both small and different from one target to another. Consequently, assay conditions must be varied for different target-probe combinations, whereas common assay conditions are desirable from the standpoint of those performing assays and from the standpoint of those developing and marketing assays and kits. Moreover, even with adjusted conditions, it is difficult to discriminate between alleles with unstructured oligonucleotide probes. It is difficult to distinguish between alleles differing by a single base pair simply according to differences in hybridization of an oligonucleotide. Further discrimination techniques, such as ligating adjacently hybridized probes at the point of mutation (Landegren et al. U.S. Pat. No. 4,988,617) or digestion and electrophoresis of the product of amplification by the polymerase chain reaction (Mullis et al. U.S. Pat. No. 4,683,195) have been developed to discriminate between alleles. However, these ligation or digestion methods have the disadvantage of requiring additional reagents or steps, or both.

It is an object of the present invention to overcome the limitations, discussed above, of conventional hybridization probes and assays and of existing homogeneous hybridization probes and assays.

Another object of this invention is hybridization probes that generate a signal upon hybridization with a target nucleic acid sequence but exhibit little or no signal generation when unhybridized, and assays using these probes.

Further objects of this invention are kits that can be used to make such nucleic acid probes specific for target sequences of choice.

A further object of this invention is homogeneous assays using such probes.

A further object of this invention is hybridization probes and rapid methods wherein detection is performed quickly and without delay.

A further object of this invention is hybridization probes and methods that can detect nucleic acids in vivo.

A further object of this invention is hybridization probes and methods that can detect nucleic acids in situ.

A further object of this invention is hybridization probes and methods that can detect nucleic acid target sequences in nucleic acid amplification and other synthesis reactions in real-time mode.

A further object of this invention is hybridization probes and assays that permit detection of nucleic acid targets without the use of expensive equipment.

A further object of this invention is labeled hybridization probes with improved ability to discriminate between genetic alleles and other closely related nucleic acid sequences, including sequences differing by only one nucleotide, and assays using such probes.

A further object of this invention is labeled hybridization probes whose construction can be modified for improved allele-discrimination in a wide range of assay conditions or using easily standardized hybridization conditions.

In order to realize the full potential of the process of hybridization in the field of diagnostics and research, a technique is needed for monitoring hybridization in solutions with probes having little or no signal of their own yet producing a detectable signal when hybridized to a target. Preferably, the probe should permit monitoring of the progress of reactions that produce nucleic acids with either linear or exponential kinetics. Also, the probe should allow detection of nucleic acids in vivo (and in situ) without the destruction of the tissue or cell. Of course, the probe should also be useful in conventional hybridization assays. Additionally, the assays should permit very sensitive detection of targets either directly or in conjunction with amplification techniques. Also preferably, the probe should be capable of generating a hybridization signal detectable by the naked eye. Finally, the probes should permit detection of different targets in a single assay. Objects of this invention are nucleic acid hybridization assays and probes that satisfy all or nearly all of these requirements.

SUMMARY OF THE INVENTION

Probes according to this invention are labeled probes that have a nucleic acid target complement sequence flanked by members of an affinity pair, or arms, that, under assay conditions in the absence of target, interact with one another to form a stem duplex. Hybridization of the probes to their preselected target sequences produces a conformational change in the probes, forcing the arms apart and eliminating the stem duplex. Embodiments of probes according to this invention employ interactive labels, whereby that conformational change can be detected, or employ a specially limited allele-discriminating structure, or both.

The invention includes conformationally detectable hybridization probes, assays and kits. It also includes universal stems and kits including said stems for making probes.

Probes according to this invention having interactive labels are "unitary", by which we mean either bimolecular probes linked as a pair and operable in an assay as linked, or unimolecular, single strands. They comprise at least: a single-stranded nucleic acid sequence that is complementary to a desired target nucleic acid, herein referred to as a "target complement sequence;" 5' and 3' regions flanking the target complement sequence that reversibly interact by means of either complementary nucleic acid sequences or by attached members of another affinity pair; and interactive label moieties for generating a signal. Preferred probes of this invention include complementary nucleic acid sequences, or "arms," that reversibly interact by hybridizing to one another under the conditions of detection when the target complement sequence is not bound to the target. Where the unitary probe is unimolecular, all the above components are in one molecule. All allele-discriminating embodiments are unimolecular. When the unitary probe is bimolecular, half, or roughly half, of the target complement sequence, one member of the affinity pair and one member of the label pair are in each molecule.

The signal generating label moieties of probes according to this invention having interactive labels are "pairs" matched such that at least one label moiety can alter at least one physically measurable characteristic of another label moiety when in close proximity but not when sufficiently separated. The label moieties are conjugated to the probe such that the proximity of the label moieties to each other is regulated by the status of the interaction of the affinity pair. In the absence of target, the label moieties are held in close proximity to each other by the linking interaction of the affinity pair. We refer to this conformation as the "closed" state. When the target-indicating detectable signal is not generated in the closed state, which is the fact with most embodiments, we say that the closed state is the "off" state.

When the target complement sequence hybridizes to its target, a conformational change occurs in the unitary probe, separating the affinity pair and, consequently, the label moieties of interactive labels. We refer to this conformation as the "open" state, which in most embodiments is the "on" state. Separation is driven by the thermodynamics of the formation of the target complement sequence-target sequence helix. Formation of the target complement sequence-target sequence helix, whether complete or nicked, overcomes the attraction of the affinity pair under assay conditions. A signal is generated because the separation of the affinity pair alters the interaction of the label moieties and one can thereafter measure a difference in at least one characteristic of at least one label moiety conjugated to the probe. An important feature of the probes of this invention is that they do not shift to the open conformation when non-specifically bound.

Probes according to this invention having interactive labels have a measurable characteristic, which we sometimes refer to as a "signal", that differs depending on whether the probes are open or closed. The measurable characteristic is a function of the interaction of the label moieties and the degree of interaction between those moieties varies as a function of their separation. As stated, unitary probes according to this invention have a closed conformation and an open conformation. The label moieties are more separated in the open conformation than in the closed conformation, and this difference is sufficient to produce a detectable change in at least one measurable characteristic. In the closed conformation the label moieties are "proximate" to one another, that is, they are sufficiently close to interact so that the measurable characteristic differs in detectable amount, quality, or level, from the open conformation, when they do not so interact. It is desirable, of course, that the difference be as large as possible. In some cases it is desirable that in the "off" state the measurable characteristic be a signal as close as possible to zero.

The measurable characteristic may be a characteristic light signal that results from stimulating at least one member of a fluorescence resonance energy transfer (FRET) pair. It may be a color change that results from the action of an enzyme/suppressor pair or an enzyme/cofactor pair on a substrate to form a detectable product. In all of these cases, we say that the probes have a characteristic signal whose level depends on whether the label moieties are proximate due to the probes being in the closed position or are separated due to the probes being in the open position.

As stated, a detectable signal may be generated by the probe in either the open or closed conformation. The choice of label moieties dictates in which state a signal is generated or that different signals are generated in each state. Our most preferred interactive label moieties are a fluorophore/quencher pair, preferably covalently conjugated to the probe, most preferably to arm portions that are not complementary to the target. Our most preferred probes thus generate a positive fluorescent signal of a particular wavelength when bound to the target in the open state and stimulated with an appropriate light source. When referring to these probes we also refer to this conformation as the "on" state.

The invention also includes "universal stems" and kits containing them. A universal stem according to this invention may be used to construct probes according to this invention for the detection of one or another target sequence by ligating or otherwise covalently linking to the universal stem an oligonucleotide or oligonucleotides containing a sequence complementary to the desired target sequence.

The invention further comprises assay methods which utilize at least one interactively labeled, unitary probe according to this invention. Such assays of this invention may be used for targets that are single-stranded or double-stranded. However, for assays that include a step or steps that may separate the affinity pair in a target-independent manner, only unimolecular probes are suitable. Assays according to this invention may be performed in vitro or in vivo. Such assays may be performed in situ in living or fixed tissue without destruction of the tissue. Preferred are assays that do not require separation or washing to remove unbound probes, although washing may improve performance. Our most preferred assays using interactively labeled, unitary probes are homogeneous assays.

Assays according to this invention using interactively labeled probes comprise at least adding at least one unitary probe according to this invention to a sample suspected to contain nucleic acid strands containing a target sequence, under assay conditions appropriate for the probe, and ascertaining whether or not there is a change in the probe's measurable characteristic as compared to that characteristic under the same conditions in the absence of target sequence. The assays may be qualitative or quantitative. In some embodiments, it may be desirable to run a control containing no target and to compare the response of the sample to the response of the control. The level of signal may be measured for quantitative determinations. A change may simply be detected for qualitative assays. When a control is used, the difference in signal change between the sample and the control may be calculated.

Assays according to this invention using probes with interactive labels may include contacting at least one unimolecular probe of the invention with amplification or other nucleic acid synthesis reactions, for example: polymerase chain reactions, PCR, (Erlich et al., 1991); Q-beta replicase-mediated amplification reactions, (Lomeli et al., 1989); strand-displacement amplification reactions, SDA, (Walker et al., 1992); self-sustained sequence reactions, 3SR, (Guatelli et al., 1990); and transcription and replication reactions. Bimolecular probes, as stated above, are not suitable for use in any reaction, e.g., PCR, in which the affinity pair would be separated in a target-independent manner; but they may be used in other reactions, e.g., transcription. In any such reaction we prefer unimolecular probes, however. These assays may be qualitative or quantitative. They may detect synthesized target in real-time mode. Of course, either unimolecular or bimolecular probes of the invention can be used in assays of completed reactions.

We refer to certain embodiments of nucleic acid probes according to this invention as "allele-discriminating" probes. These are labeled, unimolecular probes having relatively short target complement sequences flanked by nucleic acid arms that are complementary to one another. Allele-discriminating embodiments preferentially hybridize to perfectly complementary target sequences. They discriminate against sequences that vary by as little as one internally located nucleotide, which for these probes are non-targets. Allele-discriminating embodiments may include interactive labels, in which case the probes are a subset of the interactively labeled probes whose construction, operation and use in assays is described above. However, allele-discriminating probes of this invention may have labels that are not interactive, such as, for example, radioactive labels, in which case signal level does not differ depending on whether probes are open or closed. When non-interactive labels are used, bound (hybridized to target sequence) and unbound probes must be separated. Numerous techniques for separating bound and unbound (not hybridized) probes are well known to persons skilled in the art of nucleic acid hybridization assays.

Allele-discriminating probes according to this invention, both probes with interactive labels and probes with non-interactive labels, have a superior ability to discriminate between target sequences and non-target sequences differing by a single nucleotide as compared to labeled nucleic acid hybridization probes that are not structured. They also have a larger permissible range of assay conditions for proper functioning. Additionally, their performance under particular conditions can be adjusted by altering the construction of their stem duplex, a design variable not possessed by oligonucleotide probes generally. The improved characteristics of allele-discriminating probes according to this invention permit multiple assays under common conditions and multiplexed assays including multiple probes and targets in the same assay.

Assays according to this invention employing allele-discriminating probes are particularly useful to determine the allelic status of a plant or a human or other animal. They are also useful to discriminate between or among closely related viruses, bacteria and other organisms, for example, species, subspecies and variants. Embodiments of assays utilizing interactively labeled allele-discriminating probes are a subset of assays, described above, using interactively labeled probes. Embodiments of assays utilizing non-interactively labeled probes, on the other hand, include traditional separation techniques. These embodiments may include, for example, adding at least one unimolecular probe having non-interactive labels according to this invention to a sample suspected to contain nucleic acid strands containing a target sequence under assay conditions appropriate for the probe, removing unhybridized probes, and ascertaining whether or not the non-interactive signal is present. A positive or negative control may be employed. The level of non-interactive signal may be measured for quantitative determinations or a change in signal level may be detected for qualitative determinations. When a control is used, the difference between the control and the non-interactive signal may be calculated.

This invention also provides a means for locating and isolating amplified target. For example, utilizing a preferred probe comprising a fluorophore/quencher label pair, PCR products can be identified, quantified and, optionally, isolated after electrophoresis in a gel by stimulating the hybridized probe in the gel, any resulting signal indicating the presence, amount and location of the target. Similarly, this invention provides a means for identifying and, optionally, isolating any desired nucleic acid from a mixture of nucleic acids that is separated by physical means, as by chromatography or electrophoresis.

The invention also includes kits of reagents and macromolecules for carrying out assays according to this invention.

In this description we sometimes refer to "probe," "target," "oligonucleotide," "nucleic acid", "strand" and other like terms in the singular. It will be understood by workers in the art that many terms used to describe molecules may be used in the singular and refer to either a single molecule or to a multitude. For example, although a target sequence may be detected by a probe in an assay (and in fact each individual probe interacts with an individual target sequence), assays require many copies of probe and many copies of target. In such instances, terms are to be understood in context. Such terms are not to be limited to meaning either a single molecule or multiple molecules.

DETAILED DESCRIPTION OF THE INVENTION

Hybridization probes of the invention can be made from DNA, RNA, or some combination of the two. The probes may include modified nucleotides. Modified internucleotide linkages are useful in probes comprising deoxyribonucleotides and ribonucleotides to alter, for example, hybridization strength and resistance to non-specific degradation and nucleases. The links between nucleotides in the probes may include bonds other than phosphodiester bonds, for example, peptide bonds. Modified internucleotide linkages are well known in the art and include methylphosphonates, phosphorothioates, phosphorodithionates, phosphoroamidites and phosphate ester linkages. Dephospho-linkages are also known, as bridges, between nucleotides and include siloxane, carbonate, carboxymethyl ester, acetamidate, carbamate, and thioether bridges. "Plastic DNA," having for example N-vinyl, methacryloxyethyl, methacrylamide or ethyleneimine internucleotide linkages can also be used in probes (see e.g. Uhlmann and Peyman (1990) pp. 545–569) "Peptide Nucleic Acid" (PNA) is particularly useful because of its resistance to degradation by nucleases and because it forms a stronger hybrid with natural nucleic acids. (Orum et al. (1993); Egholm, et al. (1993) herein incorporated by reference).

Figure 1:
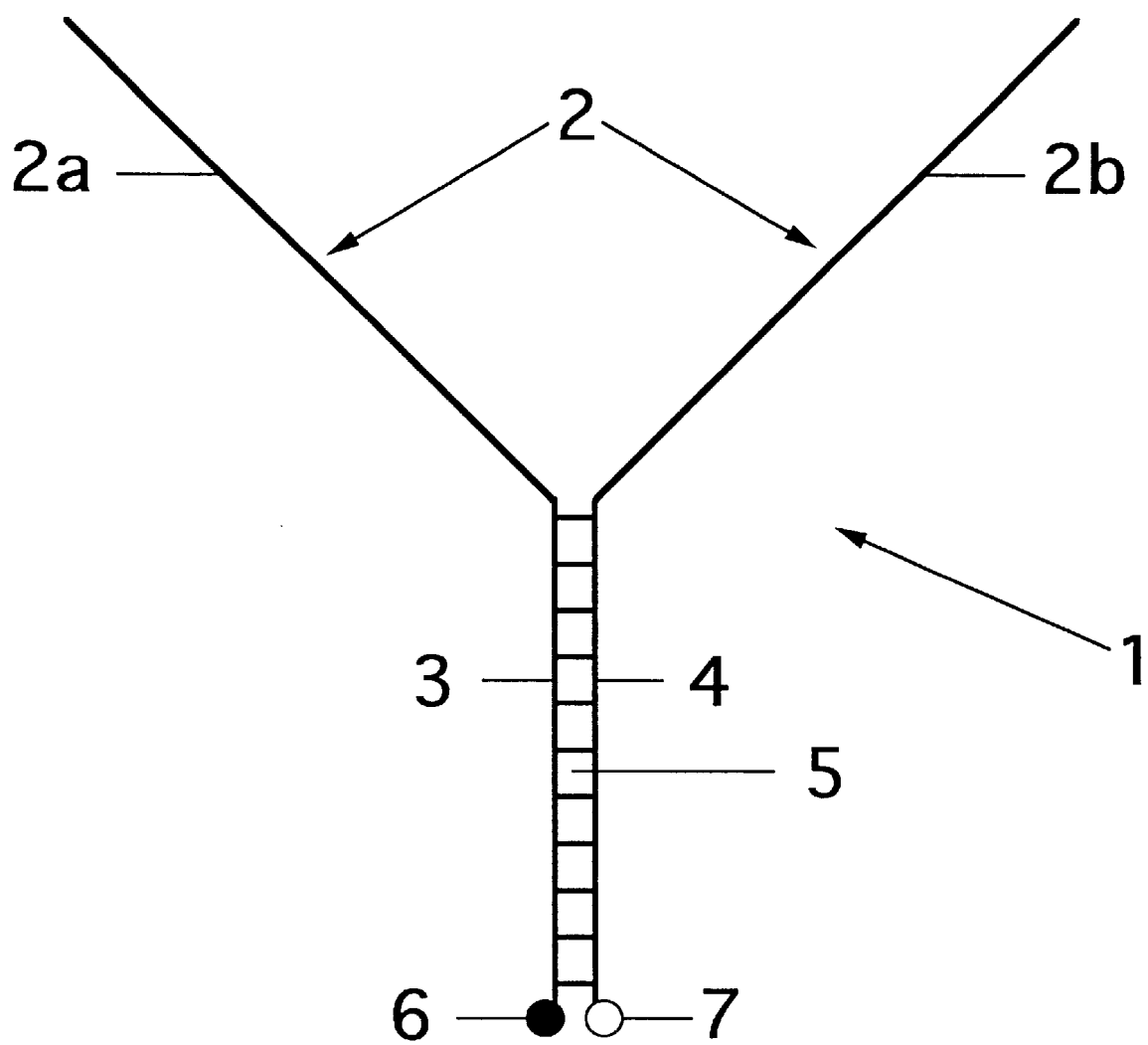
FIG. 1 is a schematic representation of a preferred bimolecular probe having interactive labels according to the invention in the "closed" conformation.

FIG. 1 schematically shows a bimolecular version of unitary probe 1 with interactive labels. Probe 1 includes a single-stranded target complement sequence 2 having a 5' terminus and a 3' terminus, which in bimolecular probe 1 includes sequence 2a and sequence 2b, which together are complementary to a preselected target sequence contained within a nucleic acid target strand. Probe 1 can be considered as a single strand, the unimolecular version, in which a single target complement sequence 2 is severed at about its midpoint. The following description describes probe 1 as so considered, that is, as the unimolecular version, for convenience. The description thus applies to both the bimolecular and unimolecular versions.

Extending from sequence 2, and linked thereto, are an affinity pair, herein depicted as oligonucleotide arms 3, 4. An affinity pair is a pair of moieties which have affinity for each other. Although we prefer complementary nucleic acid sequences, as shown in FIG. 1, other affinity pairs can be used. Examples include protein-ligand, antibody-antigen, protein subunits, and nucleic acid binding proteins-binding sites. Additional examples will be apparent to those skilled in the art. In some cases, use of more than one affinity pair may be appropriate to provide the proper strength to the interaction. The affinity pair reversibly interacts sufficiently strongly to maintain the probe in the closed state under detection conditions in the absence of target sequence but sufficiently weakly that the hybridization of the target complement sequence and its target sequence is thermodynamically favored over the interaction of the affinity pair. This balance allows the probe to undergo a conformational change from the closed state to the open state. Additionally, the affinity pair should separate only when probe binds to target and not when probe is non-specifically bound.

Figure 2:
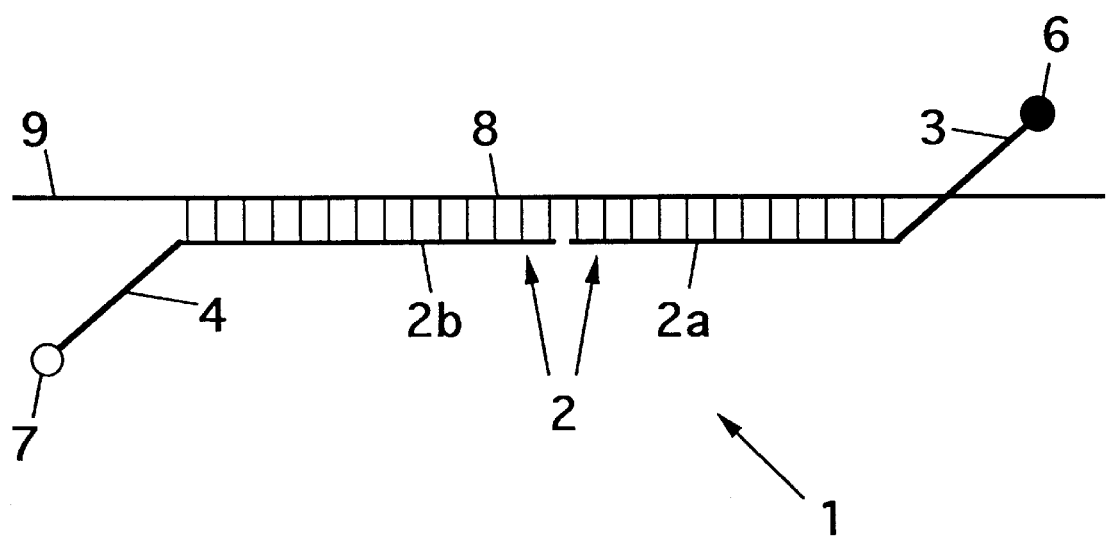
FIG. 2 is a schematic representation of a probe of FIG. 1 in the "open" conformation.

The mechanism by which the probe shifts from a closed to an open conformation will be described for the embodiment in which the affinity pair is complementary oligonucleotide arms, but the generalization to other affinity pairs will be apparent. Referring to FIG. 1, arms 3, 4 are chosen so that under preselected assay conditions, including a detection temperature, they hybridize to each other, forming stem duplex 5, which we sometimes refer to as an arm stem. In the absence of target, association of arms 3, 4 is thermodynamically favored and maintains stem duplex 5, holding the probe 1 in the closed conformation depicted in FIG. 1. In FIG. 2, target complement sequence 2 (comprising sequences 2a and 2b) is hybridized to target sequence 8 of target nucleic acid 9. That hybridization forms a relatively rigid double-helix of appropriate length. For the bimolecular version of the probe with interactive labels depicted in FIG. 2, it is a nicked helix. For probes of this invention formation of a helix by interaction of the target complement sequence and the target sequence is thermodynamically favored under assay conditions at the detection temperature and drives the separation of arms 3, 4, resulting in dissolution of stem duplex 5 and the maintenance of the open conformation depicted in FIG. 2. Arm regions 3 and 4 do not interact with each other to form the stem duplex when target complement sequence 2 is hybridized to the target sequence 8. Because the interaction of the target complement sequence 2 with the target sequence 8 drives the separation of the arms 3 and 4, we sometimes refer to this mechanism as a "spring." For certain embodiments of interactively labeled probes that are not allele-discriminating probes, the shift from the closed conformation to the open conformation occurs when the target complement sequence hybridizes to the target sequence despite the presence of a nick or the presence of one or more nucleotide mismatches. Importantly, non-specific binding of the probe does not overcome the association of the arms in this manner. This feature leads to very low background signal from inappropriately "opened" probes.

The affinity pair illustrated in the preferred embodiment of FIGS. 1 and 2 is a pair of complementary nucleic acid sequences. Arms 3, 4 are chosen so that stem duplex 5 (FIG. 1) is a smaller hybrid than the hybrid of target complement sequence 2 and target sequence 8 (FIG. 2). In the bimolecular version, stem duplex 5 should be smaller than either portion of the nicked helix that includes 2a or 2b. If that limitation is satisfied, we say that each of 2a and 2b contains "approximately half" of target complement sequence 2. Other affinity pairs, as indicated, may be conjugated to the target complement sequence, in some cases through non-complementary arms or to non-nucleic acid arms. Appropriate affinity pairs may be conjugated to the target complement sequence by methods known in the art. We prefer that the affinity pair be covalently linked directly to the target complement sequence.

A unitary probe having interactive labels according to this invention has a measurable characteristic, which we sometimes call a characteristic signal or simply the signal, due to the label pair. Probe 1 includes label moieties 6, 7 conjugated to and forming part of probe 1 at the 5' and 3' termini, respectively, of the stem duplex 5. Label moieties 6, 7 are placed such that their proximity, and therefore their interaction with each other, is altered by the interaction of arms 3, 4. Label moieties 6, 7 could be conjugated elsewhere to arms 3, 4 or to sequence 2 near its linkage with the stem 5, that is, close to arms 3, 4. Some label moieties will interact to a detectably higher degree when conjugated internally along the arms. This is because they will not be affected by unraveling of the termini.

More than one pair of label moieties may be used. Further, there is no requirement for a one-to-one molecular correspondence between members of a label pair, especially where one member can affect, or be affected by, more than one molecule of the other member. Label moieties suitable for use in probes of this invention interact so that at least one moiety can alter at least one physically measurable characteristic of another label moiety in a proximity-dependent manner. The characteristic signal of the label pair is detectably different depending on whether the probe is in the open conformation or the closed conformation.

For example, referring to FIGS. 1 and 2, the preferred label moieties are a FRET pair, most preferably fluorophore 7 and quencher 6. In that embodiment, the characteristic signal is fluorescence of a particular wavelength. When probe 1 is in the closed state (FIG. 1), label moiety 6 quenches fluorescence from moiety 7. When moiety 7 is stimulated by an appropriate frequency of light, a fluorescent signal is generated from the probe at a first level, which may be zero. Probe 1 is "off." When probe 1 is in the open state (FIG. 2), label moiety 6 is sufficiently separated from label moiety 7 that fluorescence resonance energy transfer between them is substantially, if not completely, precluded. Label moiety 6 is therefore unable to quench effectively the fluorescence from label moiety 7. If moiety 7 is stimulated, a fluorescent signal of a second level, higher than the first is generated. Probe 1 is "on." The difference between the two levels of fluorescence is detectable and measurable. Utilizing fluorescent and quencher moieties in this manner, the probe is only "on" in the "open" conformation and indicates that the probe is bound to the target by emanating an easily detectable signal. The conformational state of the probe alters the signal generated from the probe by regulating the interaction between the label moieties.

In embodiments wherein the affinity pair is complementary oligonucleotide arms, lengths of target complement sequences and arm sequences are chosen for the proper thermodynamic functioning of the probe under the conditions of the projected hybridization assay. Persons skilled in hybridization assays will understand that pertinent conditions include probe, target and solute concentrations, detection temperature, the presence of denaturants and volume excluders, and other hybridization-influencing factors. The length of a target complement sequence can range from 7 to about 140 nucleotides, preferably from 10 nucleotides to about 140 nucleotides. If the probe is also an allele-discriminating probe, the length is more restricted, as is discussed later. For bimolecular embodiments, each portion of the target complement sequence should have a length of at least 10 nucleotides. The lower limit is set by the minimum distance at which there is no detectable difference in the measurable characteristic (or characteristic signal) affected by the interaction between the label moieties used when the probe is closed, from when the probe is opened. Thus, the minimum length of the target complement sequence 2 for a particular probe depends upon the identity of the label pair and its conjugation to the probe. Our most preferred label moieties are the fluorescent moiety 5-[(2-aminoethyl)amino]naphthalene-1-sulfonic acid (EDANS) and quenching moiety 4-(4-dimethylaminophenylazo) benzoic acid (DABCYL). For EDANS and DABCYL, quenching is essentially eliminated by a separation of 60 Angstroms, which is equivalent in length to about 20 nucleotide pairs in a double-helical nucleic acid. Thus, in the preferred embodiment of FIGS. 1 and 2, target complement sequence 2, comprising 2a and 2b, should be at least 20 nucleotides long. Shortening sequence 2 will progressively weaken the signal from hybridized probes and thereby reduce the difference in signal level between open and closed probes.

The maximum length of probe embodiments that are not allele-discriminating probes is less strict and is set by the known flexibility of double-helical nucleic acid molecules (Shore et al., 1981). Because of flexibility in the probe-target hybrid, it is possible for the ends of double-helical nucleic acid molecules to touch each other if the length of the probe-target double-helix exceeds about 140 nucleotide pairs. As will be apparent to those skilled in the art, this distance may vary depending on the nucleic acids in the double-helix (DNA:DNA, DNA:RNA or RNA:RNA) and the type of double-helix formed (A-form, B-form, Z-form, etc.). For example, if the target complement sequence 2 (FIG. 1) is longer than about 140 nucleotides and binds a target to form an A-form DNA:RNA double-helix, undesirable quenching in the open conformation may occur. occasional quenching, while it may not completely destroy the ability of a probe to generate a detectable signal, tends to degrade probe performance. Undesirable quenching may be reduced by conjugating the label pair to a location other than the termini of the arms or other affinity pair.

For probes that are not allele-discriminating embodiments, the maximum length of a target complement sequence is restrained by the functional requirement that a probe assume a thermodynamically favored open conformation when bound to target. Excessively long target complement sequences form probe-target double-helices with sufficient flexibility that both the probe-target helix and the arm stem helix may be present in the same complex. The probe would then remain in the closed state. Therefore, the maximum length of the target complement sequence must be short enough, and the resulting probe-target helix thereby rigid enough, that the probe assumes an open conformation when bound to the target. For the above reasons, the maximum length of the target complement sequence should not exceed in any event about 140 nucleotides, by which we mean within ten percent of that number depending on the factors discussed above.

When designing probes with interactive labels according to this invention, whether or not allele-discriminating embodiments, consideration may be given to the helical nature of double-stranded DNA. When a unimolecular probe is in the open conformation, maximum separation of label moieties is achieved if the moieties are located on opposite sides of the probe-target double-helix. For example, if the label moieties are conjugated to the 5' and 3' termini of the stem duplex distal to the target complement sequence linkage, and a B-form target complement sequence-target double-helix is expected, the choice of a 6-, 16-, 26-, 37-, 47-, 58-, 68-, or 79-nucleotide-long target complement sequence will achieve maximum separation by orienting the label moieties in a trans configuration on opposite sides of the double-helix, as label moieties 6, 7 are shown in FIG. 2. In this size range, we prefer target complement sequences which are within 1 to 3 nucleotides of these lengths. We prefer a target complement sequence having a length in the range of 7 to 60 nucleotides, preferably 10–40. The target complement sequences of our most preferred embodiments constructed to date are 15 and 35 nucleotides.

In preferred embodiments having nucleic acid sequences as the affinity pair, the arm sequences should be of sufficient length that under the conditions of the assay and at the detection temperature, when the probe is not bound to a target, the arms are associated, and the label moieties are kept in close proximity to each other. Depending upon the assay conditions used, 3–25 nucleotide arm lengths can perform this function. An intermediate range of 4–15, and more preferably 5–11, nucleotides is often appropriate. The actual length will be chosen with reference to the target complement sequence such that the probe remains in the closed conformation in the absence of target and assumes an open conformation when bound to target. As the target complement sequence increases in size up to 100 nucleotides, the arm length may increase up to 15–25 nucleotides. Above a 100 nucleotide-long target complement sequence, the arm length is not increased further. If the probe is also an allele-discriminating probe, the arm lengths are more restricted, as is discussed later.

When oligonucleotide sequences are used as the affinity pair, the upper limit of the length of the arms is governed by two criteria related to the thermodynamics of probes according to the invention. First, we prefer that the melting temperature of the arm stem, under assay conditions, be higher than the detection temperature of the assay. We prefer stems with melting temperatures at least 5° C. higher than the assay temperature and, more preferably at least 10° C. higher.

Secondly, the energy released by the formation of the stem should be less than the energy released by the formation of the target complement sequence-target sequence hybrid so that target-mediated opening of the probe is thermodynamically favored. Thus, the melting temperature of the target complement sequence-target sequence hybrid is higher than the melting temperature of the stem. Therefore, arm sequences should be shorter than the target complement sequence. For bimolecular embodiments, as already stated, the arm sequences should be shorter than each portion of the target complement sequence.

Therefore, the melting temperature of the arm stem must be above the assay temperature, so that the probe does not open before the target complement sequence hybridizes to a target, and yet sufficiently below the melting temperature of the hybrid, complete or nicked, of the target complement sequence with the target sequence to assure proper probe functioning and, thereby, generation of a detectable signal. We prefer that the melting temperature of the arm stem be at least 5° C., more preferably at least 10° C., above the assay temperature and at least about 20° C. below the melting temperature of the hybrid of the target complement sequence with the target sequence.

Embodiments of probes according to this invention also include allele-discriminating probes, which are labeled unimolecular probes having complementary oligonucleotide arms. Allele-discriminating probes do not shift from the closed conformation to the open conformation when there is one or more internally located nucleotide mismatches between a target-like sequence and the target complement sequence. By "internally located" we mean not at a terminal or penultimate nucleotide of the target complement sequence. Allele-discriminating probes may also be used to detect internally located insertions or deletions. We prefer that the target complement sequence be designed such that the mismatch, deletion or addition occurs as close to the middle as possible. Allele-discriminating probes open and close by the same thermodynamic mechanism described above for unimolecular probes according to this invention.

However, we have discovered some additional considerations that we believe are useful in the design of allele-discriminating probes according to the present invention. Allele-discriminating probes must be designed such that, under the assay conditions used, hybridization and the shift to the open conformation will occur only when the target complement sequence finds a perfectly complementary target sequence. We believe that the intramolecular nature of the stem duplex makes formation of the stem duplex much more likely than if that formation were intermolecular. This imparts significant freedom of design and surprisingly improved discrimination power. The difference in energy released by forming a target complement sequence-perfectly complementary target sequence hybrid versus the energy that would be released in the formation of a target complement sequence-imperfectly complementary sequence hybrid must be considered with reference to the energy released in forming the stem duplex. The energy released under assay conditions in forming a perfect hybrid between the target complement sequence and the target sequence must be greater than the energy released in the formation of the stem duplex. However, the energy that would be released under the same assay conditions in forming an imperfect hybrid between the target complement sequence and a non-target sequence having one internally located mismatch must be less than the energy released in formation of the stem duplex.

A probe designed within these parameters will hybridize and shift to the open conformation only when the target sequence is a perfect complement to the target complement sequence. We have found that probes having target complement sequences from 7 to 25 nucleotides, combined with arm sequences from 3 to 8 nucleotides, may be designed within these parameters. The guanosine-cytidine content of the stem duplex and probe-target hybrids, salt, and assay temperature should all be considered. We have found that magnesium salts have has a strong stabilizing effect that is particularly important to consider when designing short, allele-discriminating probes. One may calculate the free energy released in the formation of any particular hybrid according to known methods, including the methods of Tinoco et al., (1973) and Freier et al., (1986). However, in most instances, it is simplest to approximate the energetics, synthesize a probe, and test the probe against targets and imperfect non-targets to be discriminated against, under the assay conditions to be used.

If an allele-discriminating probe is to have a target complement sequence near the upper limits of 25 nucleotides long, the sequence should be designed such that a single nucleotide mismatch to be discriminated against occurs at or near the middle of the target complement sequence. For example, probes with 21 nucleotide long probe sequences should preferably be designed so that the mismatch occurs opposite one of 14 most centrally located nucleotides of the target complement sequence and most preferably opposite one of the 7 most centrally located nucleotides. Designing a probe so that the mismatch to be discriminated against occurs in or near the middle of the target complement sequence-imperfect target sequence is believed to improve the performance of an allele-discriminating probe.

One skilled in the art will realize that these parameters will vary with the conditions of the hybridization assay and that those conditions must be considered when designing the nucleic acid sequences of probes of this invention. Put another way, the probe must be constructed to function as described above under the conditions of the assay in which it is to be used in order to be a probe according to this invention. A particular construction may be a probe according to this invention under one set of assay conditions but not under another set of assay conditions. The length of the arms and their guanosine-cytidine content affect the melting temperature of a stem duplex. For a desired melting temperature, under particular assay conditions, a length and a guanosine-cytidine content of the arms can easily be calculated by those skilled in the art. The melting temperature of the duplex stem of a probe can be empirically determined for given assay conditions using the methods described below in Example V.

We view these parameters as design considerations which are useful as guidelines. Because the behavior of probes in complex solutions can not always be predicted with certainty, empirical testing is very useful in tailoring probes according to the invention to perform optimally under particular assay conditions, that is, to maximize the off versus on signal difference and, if desired, to minimize the off signal level.

As is apparent to one skilled in the art from the foregoing descriptions of probe function, the thermodynamics of probes having nucleic acid stems will vary with length and nucleotide composition of the stem and target complement sequence, as well as assay conditions. An advantage of the present probes over "linear" oligonucleotide probes, by which we mean probes having no closed conformation, is that one has much greater latitude to design probes according to the assay conditions, rather than, as typically done, to vary assay conditions to suit a linear oligonucleotide probe. When one attempts to discriminate between perfectly complementary targets and non-targets having a single mismatch with a linear oligonucleotide probe, one must attempt to find a narrow range of assay conditions wherein the linear oligonucleotide will hybridize only to a perfectly complementary target sequence. In contrast, formation of the stem duplex of an allele-discriminating probe according to this invention provides a release of free energy countervailing the release of free energy of formation of a mismatched hybrid with the target complement sequence. Therefore, the presence of the stem duplex prevents the formation of a mismatched hybrid under assay conditions in which a linear oligonucleotide forms a mismatched hybrid.

An allele-discriminating probe according to this invention may have interactive labels as described above. It may, however, have a non-interactive label which emits a non-interactive signal. In such probes according to this invention, the non-interactive signal can be generated irrespective of whether the probe is in the open or closed position. Non-interactive labels are commonly known in the art and include labels such as radioisotopes, enzymes such as alkaline phosphatase or horseradish peroxidase, fluorophores and label moieties for the generation of light through radioluminescent, bioluminescent, chemiluminescent or electrochemiluminescent reactions. Non-interactive label moieties may be anywhere in the probe or may be conjugated to the probe at any location, as long as probe function, particularly hybridization to target, is not substantially interfered with.

Figure 9:
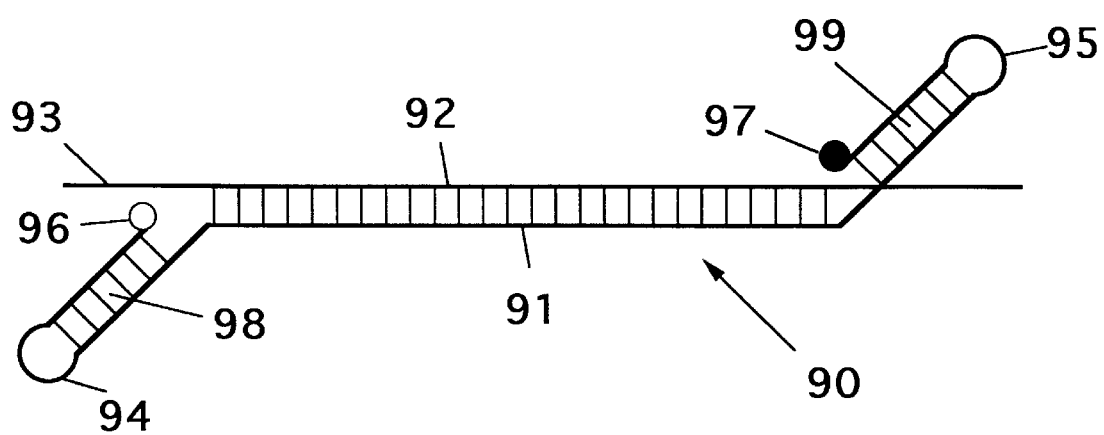
FIG. 9 is a schematic representation of a unimolecular probe with hairpin sequences in the arms, and interactive labels, bound to a target sequence.

In certain preferred embodiments the sequence of each arm forms an internal secondary structure, such as a hairpin stem, when the probe is open. A unitary probe 90 of this design, having interactive labels, is illustrated in FIG. 9. Probe 90 is unimolecular, but this design feature applies to bimolecular probes as well. Once target complement sequence 91 has bound to the target sequence 92 of target 93 and formed a probe-target helix, arms 94, 95 are separated, and a signal is generated by separation of label moieties 96, 97. The open conformation shown in FIG. 9 is stabilized because the opened arms 94, 95 fold back on themselves to form hairpins 98, 99. The hairpins are comprised of neighboring complementary sequences that form a stem that is at least three nucleotide pairs in length. This stabilizes the open conformation, because additional energy is released when each separated arm 94, 95 forms an internal hairpin structure. Additionally, arms containing these hairpin structures are effectively shortened and are thus less likely to interact with each other. With this feature it may be possible to use arms, within the 10–25 nucleotide range, that are relatively longer than would be appropriate for arms without this feature, to hold the label moieties more tightly together in the closed conformation. Consequently, probes with this feature may exhibit a sharper signal because of a lower level of background in the closed conformation.

Another means of stabilizing the open conformation is to have one or both arm sequences be at least partially complementary to sequences adjacent to the target sequence. Complementary sequences may be placed within an arm at locations proximal or distal to the junction of the arm and target complement sequence. Further, one arm sequence may be completely complementary to sequences adjacent to the target without putting undue restriction on the design of a probe tailored to a specific target. This feature increases the thermodynamic stability of the open conformation. We note that although portions of the arms may be complementary to the target, interaction of the target complement sequence with the target sequence must be sufficient to shift the probe to the open conformation. This design feature applies both to unimolecular embodiments and bimolecular embodiments.

FIGS. 1–5 show our preferred label pair as a luminescent moiety (7, 37, 46, 55) and a quenching moiety (6, 38, 45, 56). Any label pair can be used to generate a signal where one member of the pair can detectably alter at least one physically measurable characteristic of the other when in close proximity, but to a different extent when apart. Alternatively, both members may detectably alter such a characteristic of one member when in close proximity, but differently when apart. Additionally, it is necessary that the label moieties must be conjugatable to the probe.

Luminescent label moieties to be paired with appropriate quenching moieties can be selected from any one of the following known categories: a fluorescent label, a radioluminescent label, a chemiluminescent label, a bioluminescent label and an electrochemiluminescent label. The use of multiple quenching moieties with a single luminescent moiety will increase quenching. In this instance a label pair comprises one fluorescent moiety "paired" to several quenching moieties. Other useful label pairs include a reporter enzyme and appropriate inhibitor.

Although not preferred, a useful label pair may generate a signal in the closed conformation and be inactive in the open conformation. Examples of such pairs are an enzyme and its cofactor and fragments or subunits of enzymes that must be close to each other for the enzyme to be active. In embodiments of this type, the closed conformation is the "on" state.

Our preferred labels are chosen such that fluorescence resonance energy transfer is the mode of interaction between the two labels. In such cases, the measurable physical characteristics of the labels could be a decrease in the lifetime of the excited state of one label, a complete or partial quenching of the fluorescence of one label, an enhancement of the fluorescence of one label or a depolarization of the fluorescence of one label. The labels could be excited with a narrow wavelength band of radiation or a wide wavelength band of radiation. Similarly, the emitted radiation could be monitored in a narrow or a wide range of wavelengths, either with the aid of an instrument or by direct visual observation. Examples of such pairs are fluorescein/sulforhodamine 101, fluorescein/pyrenebutanoate, fluorescein/fluorescein, acridine/fluorescein, acridine/sulforhodamine 101, fluorescein/ethenoadenosine, fluorescein/eosin, fluorescein/erythrosin and anthranilamide-3-nitrotyrosine/fluorescein. Other such label pairs will be apparent to those skilled in the art.

Our most preferred probes, both unimolecular and bimolecular, described more particularly in the Examples, allow detection of hybridization by the naked eye and require only a simple ultraviolet lamp as an excitation device. These probes satisfy the following criteria: only one label moiety is fluorescent, and its fluorescence is visible to the naked eye; the other label moiety quenches this fluorescence extremely efficiently; and no significant quenching occurs at distances greater than about two turns of a nucleic acid double-helix. Of course, multiple copies of one or both label moieties may be used.

Our most preferred fluorescent label is EDANS and our most preferred quenching moiety is DABCYL. The absorption spectrum of DABCYL has a good overlap with the emission spectrum of EDANS, leading to very efficient energy transfer. It has been shown that one can achieve a 40-fold reduction in the fluorescence of EDANS by linking it to DABCYL through an octapeptide spacer, and more than a 200-fold reduction in fluorescence by linking EDANS directly to DABCYL. Also, there is no quenching of the fluorescence of EDANS by DABCYL at distances greater than 60 Angstroms. Finally, DABCYL has no fluorescence of its own (Matayoshi et al., 1990; Wang et al., 1991).

EDANS and DABCYL are conjugated to the probe in the region of the oligonucleotide arms or other affinity pair. In our most preferred probes to date, both unimolecular and bimolecular, EDANS and DABCYL are covalently linked to the free 5' and 3' termini of the arms, distal to the linkage of the arms and the target complement sequence. The positions of EDANS and DABCYL at, respectively, the 5' and the 3' termini can, of course, be reversed. The EDANS and DABCYL moieties could be conjugated anywhere along the terminal portions of the probe, as long as they are proximate to each other in the closed conformation of the probe and sufficiently separated from each other in the open conformation. We sometimes refer to a probes so labeled as oppositely terminally labeled probes.

Referring to FIG. 1, locating the label moieties along the stem duplex 5, rather than at the free 5' and 3' termini of the arms, may increase the interaction between the label moieties when the probe is in the closed conformation. It is well known that the terminal nucleotides of a double-helix will unravel and rehybridize in a random fashion at a rate dependent on temperature. Therefore, placing the moieties internally along the stem will result in less separation of the moieties due to the unraveling of the termini.

When placing moieties along the stem duplex, consideration may be given to the helical structure of the stem duplex. The moieties may be conjugated to nucleotides staggered along each arm such that when the arms anneal, the moieties will lie on the same side of the stem-duplex helix. This positioning will further maximize interaction of the label moieties in the closed conformation.

As stated earlier, multiple labels, e.g., multiple EDANS and DABCYL moieties, can be used. Multiple labels, in some cases, permit assays with higher sensitivity. For example, when the affinity pair is oligonucleotide arms, a multiplicity of labels can be achieved by distributing a number of EDANS moieties on one arm and a corresponding number of DABCYL moieties on the other arm, such that each EDANS moiety can be close to a DABCYL moiety when the arm stem helix forms. Multiplicity can also be achieved by covalently linking multiple labels to the arms, in a manner resembling a bunch of grapes. A multiplicity of labels should not be used with label moieties that self-quench. In a preferable application, quenching in the closed conformation may be enhanced by placing a single EDANS moiety on one arm and multiple DABCYL moieties on the other arm such that when the stem helix is formed, at least one DABCYL moiety is adjacent to an EDANS moiety at any given instant.

The conjugation of the label moieties to any location on the probe must be stable under the conditions of the assay. Conjugation may be covalent, which we prefer. Examples of noncovalent conjugation include, without limitation, ionic bonding, intercalation, protein-ligand binding and hydrophobic and hydrophilic interactions. Appropriately stable means of association of label moieties to the probes will be apparent to those skilled in the art. The use of the term "conjugation" herein encompasses all means of association of the label moieties to the probe which are stable under the conditions of use. We consider stably conjugated label moieties to be included within the probe molecule to which they are conjugated.

We sometimes conjugate label moieties to the probes by covalent linkage through spacers, preferably linear alkyl spacers. The nature of the spacer is not critical. For example, EDANS and DABCYL may be linked via six-carbon-long alkyl spacers well known and commonly used in the art. The alkyl spacers give the label moieties enough flexibility to interact with each other for efficient fluorescence resonance energy transfer, and consequently, efficient quenching. The chemical constituents of suitable spacers will be appreciated by persons skilled in the art. The length of a carbon-chain spacer can vary considerably, at least from 1 to 15 carbons. However, in the case of multiple labels conjugated to an arm in a "bunch of grapes" configuration, a multiply bifurcated spacer is desirable.

For allele-discriminating probes that have non-interactive labels, labels may be conjugated to the probes as described above. However, radioactive labels may be incorporated in the probes by synthesis with radioactive nucleotides or by a kinase reaction, as is known in the art.

The hybridization probes and universal stems of this invention may comprise nucleic acid molecules that can be assembled by commonly known methods of solid-phase synthesis, by ligation of synthetic sequences or restriction fragments or by a combination of these techniques. The simplest probes can be assembled by synthesis of a single oligonucleotide comprising arm sequences flanking the target complement sequence. Label moieties are then conjugated to the termini of the oligonucleotide. Alternatively, labeled nucleotides can be used in oligonucleotide synthesis. A bimolecular probe may be prepared as two separately synthesized, labeled oligonucleotides. A bimolecular probe can be converted to the corresponding unimolecular probe by linking the target complement sequence portions, as by ligation on a splint. Direct synthesis is particularly appropriate in cases where it can be performed with acceptable yield.

One use of a combination of synthesis and ligation is illustrated by the assembly of a unimolecular DNA probe from two directly synthesized oligodeoxynucleotides. One oligonucleotide contains the target complement sequence, a complete first arm sequence covalently linked to one of the label moieties, and a portion of the second arm sequence. The arm and arm portion of this oligonucleotide hybridize to each other. The second oligonucleotide comprises the remainder of the second arm sequence covalently linked to the other label moiety. The second oligonucleotide is complementary to the unhybridized, or overhang region of the first. The two oligonucleotides are annealed to each other. Finally, the probe is assembled by ligation of the annealed complex.

Alternatively, two oligonucleotides are synthesized, each comprising a substantial portion, "approximately half" as we use that term, of the target complement sequence, an arm sequence located 5' on one oligonucleotide and 3' on the other and appropriate label moieties. If a unimolecular probe is desired, these two oligonucleotides are annealed across a splint oligonucleotide and ligated. The probe is then purified from the splint by gel purification or other means known in the art. If a bimolecular probe is desired, the probe is assembled by annealing the two oligonucleotides.

The present invention includes kits containing a universal stem and instructions to use the universal stem to prepare probes according to the invention for the detection of a variety of preselected target sequences. The universal stem comprises portions of arm regions, each conjugated to a member of a label pair. For use in making unimolecular probes according to this invention, a stem may be supplied and used as a unit, with the arms hybridized to each other, such that a linking end of the duplex, comprising reactive groups, is formed. Optionally, the linking end may include a ligatable blunt end or overhang. Alternatively, other biochemical linking agents, or chemical agents, may be present at the 5' and 3' linking termini of the universal stem. Chemical ligation may involve reactive groups, such as hydroxyl, phosphate, sulfhydryl, amino, alkyl phosphate, alkyl amino or hydroxy alkyl. We prefer covalently reactive groups.

Having the universal stem hybridized at the time a probe is prepared is advantageous, because that automatically avoids linking the same arm region at both ends of the probe. Alternatively, however, the universal stem need not be hybridized during probe preparation if mutually exclusive attachment reactions are used for each arm portion. In the latter case, the arm portions may be kept separated for sequential reaction, but we still refer to the arm portions as a universal stem. For use in preparing bimolecular probes, and for use in preparing unimolecular probes by ligation of bimolecular probes, we prefer that the two stem parts be supplied and used separately.

We prefer universal stems comprising oligonucleotide arm portions 5 to 20 nucleotides in length. The nucleotides of the arm portions in a universal stem according to this invention need not be involved in target sequence recognition and will not be except in special cases, as will be understood. The stem need only participate in regulating the conformational state of the unitary probe. Our preferred universal stems include FRET pairs as label moieties, most preferably EDANS and DABCYL, each conjugated to one terminus of the stem duplex, distal to the linking end, as described below. We have prepared the two universal stem oligonucleotides by solid-state synthesis. However, natural sequences of appropriate length and melting temperature may also be adapted for use as stems.

As one skilled in the art will recognize, stems possessing an oligonucleotide comprising an overhang sequence that is complementary to itself can lead to undesirable association of two stems. It is thus preferred, although not required, to avoid the use of oligonucleotides that will form such dimers.

Using a universal stem according to this invention may include synthesis of an oligonucleotide comprising a target complement sequence flanked by the remaining portions of the arm sequences of the final probe. This oligonucleotide self-hybridizes via the remaining arm portions, creating a linkable terminus. If the universal stem includes an overhang, the oligonucleotide should have an overhang complementary to the overhang on the universal stem. This oligonucleotide is then linked to the universal stem, preferably by enzymatic or chemical ligation, as described above. The universal stem is thereby incorporated into the final probe stem of a unimolecular probe according to the invention.

A universal stem according to this invention is of particular benefit to a researcher wishing to design a variety of unimolecular or bimolecular probes. Universal stems may be part of a kit comprising one or more stems and instructions for preparing appropriate target complement sequence oligonucleotides, or appropriate restriction fragments, and subsequently linking to a stem. The instructions should describe the portions of the arm sequences, if any, required to flank the target complement sequence and form the appropriate linkable terminus, described above. A kit may include multiple universal stems varying by the melting temperature and/or length of the final probe stem to be formed. A kit could have one common stem oligonucleotide and multiple versions of the other stem oligonucleotide varying in length. Thus, a kit may include stems appropriate for preparation of probes according to this invention with several lengths of target sequence or with the same target sequence for use under a variety of different preselected assay conditions. Instructions in such a kit would direct the user to the proper universal stem for use with a particular target complement sequence according to the teachings herein. Kits may also optionally include enzymes and reagents, so that the kit user may easily use the universal stems to design and prepare probes of the present invention.

Assays according to this invention, which may be qualitative or quantitative, do not require washing to remove unbound probes, if interactive labels are used. An assay according to this invention may thus comprise adding a unitary probe according to this invention to a sample suspected to contain strands containing target sequence and ascertaining whether or not a detectable signal occurs under assay conditions at the detection temperature. Homogeneous assays are preferred, although probes with interactive labels according to this invention may be used in heterogeneous hybridization assays. Assays according to this invention employing allele-discriminating probes with non-interactive labels are heterogeneous hybridization assays, that include separation or washing steps. A control without target sequence may be run simultaneously, in which case signal generation of the sample and the control may be compared, either qualitatively or quantitatively by measuring the two and calculating a difference. Assays of this invention include real-time and end-point detection of specific single-stranded or double-stranded products of nucleic acid synthesis reactions, such as transcription, replication, polymerase chain reaction (PCR), self-sustained sequence reaction (3SR), strand-displacement amplification reaction (SDA), and Q-beta replicase-mediated amplification reaction. For assays wherein the unitary probes will be subjected to melting or other denaturation, the probes must be unimolecular. Assays with allele-discriminating probes include, for example, amplifying a sequence or genomic region that contains either a target sequence or an allele of that target sequence, and adding probe to detect which allelic variant is present in the amplified product. If the probe has interactive labels, the assay can be homogeneous. If the probe has a non-interactive label, separation of bound from unbound probes is included in the assay.

Quantitative assays can employ quantitating methods known in the art. An end point for a sample may be compared to end points of a target dilution series, for example. Also, readings may be taken over time and compared to readings of a positive or negative control, or both, or compared to curves of one or more members of a target dilution series.

Assays according to the invention employing probes with interactive labels include in situ detection, qualitative or quantitative, of nucleic acids in, for example, fixed tissues without destruction of the tissue. Because a large excess of probes can be used without the need for washing and without generation of a large background signal, in situ assays of this invention are particularly useful. In situ hybridization assays, according to this invention include "chromosome painting," for the purposes of mapping chromosomes, and for detecting chromosomal abnormalities (Lichter et al., 1990).

Assays of this invention employing probes with interactive labels include in vivo assays. A large excess of probes can be used without the need to wash. The assays can be for double-stranded targets, as well as single-stranded targets. Probes according to this invention are useful as "vital stains" (agents that can stain specific constituents of cells without killing them) in assays for the detection of targets in vivo. They can be used in assays to locate specific nucleic acids within various living cells or organelles within living cells. They can be used in assays to identify specific cell types within a tissue or within a living organism. In assays according to this invention, probes can be delivered to the interior of cells via known techniques, e.g., by liposomes or by making the cell membranes porous to nucleic acid molecules. For studying gene expression during development we prefer direct injection.

By using multiple probes with interactive labels that generate different, non-interfering detectable signals, e.g., fluorescence at different wavelengths or fluorescence and colored product formation, assays of this invention can detect multiple targets in a single assay. Also, multiple probes, each specific for different regions of the same target nucleic acid, yet having the same label pair, can be used in order to enhance the signal. If multiple probes are used for the same target, they should bind to the target such that neighboring probes do not quench each other. Similarly, one can use multiple-allele-discriminating probes with different, distinguishable but non-interactive labels in assays that include separation of hybridized probes from unhybridized probes.

Additionally, special probes according to this invention can be designed to detect multiple target sequences. If multiple target complement sequences are incorporated into one probe, the probe design must be such that hybridization of any one sequence to its target causes the probe to shift from the closed conformation to the open conformation.

Certain preferred embodiments of assays according to this invention comprise addition of probes with interactive labels according to this invention to a sample and visualization with the naked eye for detection of a specific target nucleic acid sequence in a complex mixture. By comparison with positive standards or the results obtained with positive standards, visualization can be roughly quantitative. In certain situations, as where information on the size of a nucleic acid is desired, nucleic acid in the sample can first be fractionated by non-denaturing gel electrophoresis, and then the gel itself can be assayed directly. Alternatively, hybridization can be carried out on restriction fragments, either without fractionation or prior to fractionation, as in Example VI.

Thus, with this invention the need for often-used procedures such as Southern and northern blotting (Sambrook et al., 1989), can be eliminated. However, probes of the present invention are also very useful in such-heterogeneous assays. A major drawback of these assays, the requirement of extensive washing to reduce the background signal from probes which are not hybridized to targets, is ameliorated by the use of probes of the present invention with interactive labels.

Our preferred probes, both unimolecular and bimolecular, with interactive labels, emanate a high level of positive signal only in the target-bound, open conformation and little-to-no signal in the closed conformation. Furthermore, our preferred probes do not assume the open conformation unless bound to target, remaining closed when non-specifically bound. As described above, this leads to a background signal that is nonexistent or naturally very low. Therefore, the use of these probes greatly simplifies conventional, heterogeneous assays because either no washing is required or only mild, low stringency washing is used to further reduce any background signal present after hybridization. Additionally, conventional hybridizations may be carried out under generally less stringent conditions.

Heterogeneous assays according to the present invention may include the use of capture probes. In a capture-probe assay, a capture probe is attached to a surface either before or after capturing a target strand. Surface attachment means and steps are well known in the art and include reaction of biotin-labeled capture probes to avidin-coated surfaces, for example, magnetic beads. The capture probe includes a sequence complementary to a sequence in the target strand and hybridizes to the target strand to capture it. Probes according to this invention, having a target complement sequence that hybridizes to the target at a location other than the location where the capture probe hybridizes, may be added before or after or at the same time as the capture probes and before or after washing the capture probe-target strand hybrids. If a probe with interactive label moieties is used, washing is not required, although mild washing may enhance the assay result by lowering background. If a probe with a non-interactive label is added, then surface bearing the capture probe-target strand-probe hybrids should be washed as in a typical heterogeneous assay.

Probes according to the invention open very quickly upon interaction with a target sequence. The ability to interact is concentration dependent, as workers skilled in hybridization assays recognize. Assay conditions may be selected in which the probes with interactive labels respond to the presence of target nucleic acids and generate signal very quickly. Because of this, assays according to this invention include real-time monitoring of production of specific nucleic acids. Synthesis processes such as transcription, replication or amplification can be monitored by including probes in the reaction mixture and continuously or intermittently measuring the fluorescence. Probes are used in substantial excess so that the relatively abundant probes find their targets in nascent nucleic acid strands before the targets are sequestered by the binding of complementary strands.

The use of probes of this invention with interactive labels in assays for the identification of products of nucleic acid amplification reactions generally eliminates the need for post-amplification analysis to detect desired products and distinguish desired products from unwanted side reactions or background products. Of course, probes according to the invention can be added at the end of a synthesis process for end-point detection of products. In assays for monitoring the progress of an amplification reaction, the probes can be present during synthesis. The presence of probes improves the accuracy, precision and dynamic range of the estimates of the target nucleic acid concentration. Reactions in closed tubes may be monitored without ever opening the tubes. Therefore, assays using these probes with interactive labels can limit the number of false positives, because contamination can be limited.

Unimolecular probes with interactive labels according to the invention are particularly useful in assays for tracking polymerase chain reactions, since the probes according to this invention can open and close with a speed that is faster than the speed of thermal cycling. A probe, preferably one that is "off" in the closed position, and includes a target complement sequence having complementarity to an expected amplification product, is included in a polymerase chain reaction mixture. For this embodiment the probe has a melting temperature such that the probe remains closed under the reaction conditions at the annealing temperature of the polymerase chain reaction. The probe may, but need not, remain closed at the extension temperature, if that is higher than the annealing temperature. At the annealing temperature, the target complement sequence hybridizes to its target and the probe generates signal. During the ramp down from the denaturing temperature to the annealing temperature and also at the annealing temperature, melted (i.e., opened) probes which do not find their target close rapidly through an intramolecular event. The signal, e.g. fluorescence, may therefore be read at the annealing temperature. It is also possible to program into the reaction cycle a distinct temperature at which the fluorescence is read. In designing a probe for use in a PCR reaction, one would naturally choose a target complement sequence that is not complementary to one of the PCR primers.

Some probes can be displaced from their target sequence by the annealing of the product's complementary strand, as can PCR primers. This can be overcome by increasing the concentration of the probes or by designing an asymmetry into the synthesis of the product strands in the polymerase chain reaction. In asymmetric amplification, more of the strand containing the target is synthesized relative to the synthesis of the complementary strand.

Similarly, other nucleic acid amplification schemes (see Landegren, 1993, for a review) can be monitored, or assayed, with embodiments of probes of this invention with interactive labels. Appropriate probes can be used, for example, in Q-beta replicase-mediated amplification, self-sustained sequence replication, transcription-based amplification, and strand-displacement amplification reactions, without any modification in the scheme of amplification. For monitoring amplifications that utilize DNA-directed RNA polymerase, for example transcription, the probes must not be templates for the polymerase; for example, the probes can be RNA.

Figure 10:
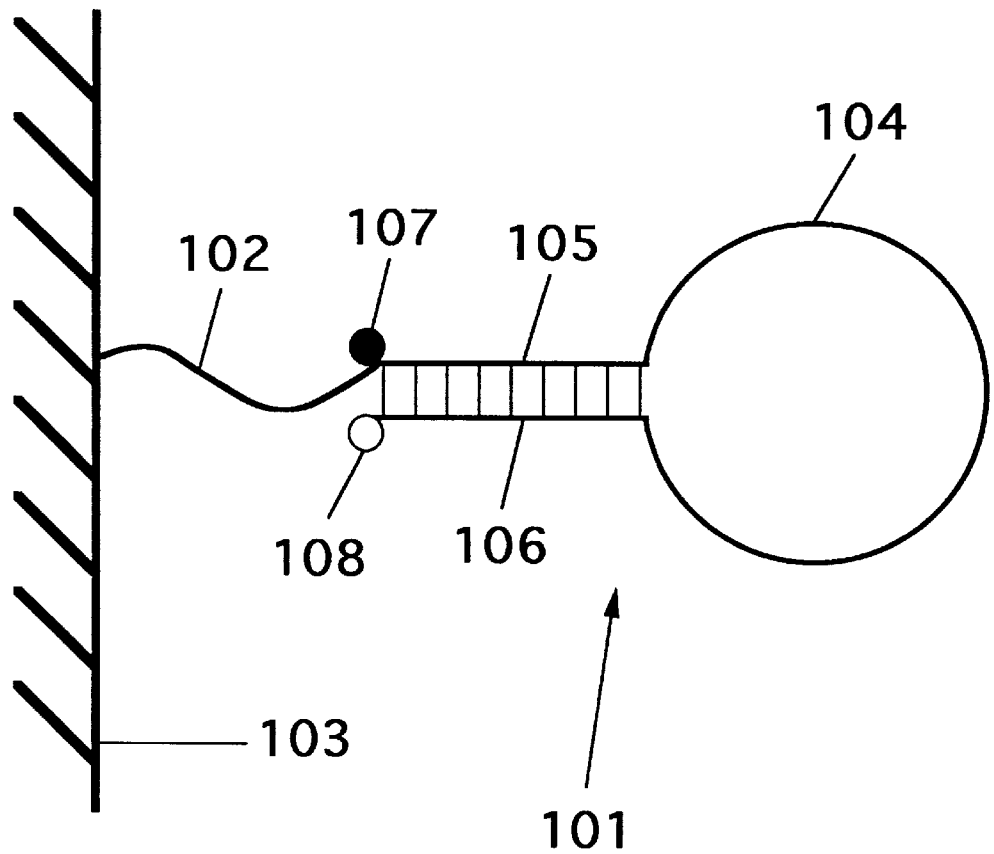
FIG. 10 is a schematic representation of a tethered unimolecular probe having interactive labels according to the invention.

Certain embodiments of assays according to the present invention utilize multiple hybridization probes with interactive labels linked to a solid surface or surfaces. Because probes of this invention are used, washing is not required. When probes are linked to a solid surface, we refer to them as "tethered probes." Tethered probes according to this invention must have interactive labels. They may, but need not be, allele-discriminating probes as well. A probe of this type is depicted in FIG. 10, which shows a probe 101 having a target complement sequence 104, complementary arms 105 and 106, and label pair 107, 108 conjugated to arms 105, 106. Probe 101 is tethered to solid surface 103 by a linking moiety 102. Linking moiety 102 may be covalent or non-covalent. We prefer covalent linkage. Any type of surface 103 may be used, including beads, membranes, microtiter wells, and dipsticks. We prefer surfaces that are neutral with respect to the components of the probe, that is, surfaces that do not interact with nucleic acids, do not interact with the label moieties and do not interfere with the probe signal. An example of such a surface is a surface coated with a siliconizing agent.

A useful surface does not significantly interfere with: a) the ability of the affinity pair, preferably arm sequences, of the probe to maintain the closed conformation; b) the hybridization of the target complement sequence to the target; c) the ability of the affinity pair to remain displaced, preferably of arm sequences of the probe to remain unhybridized to each other, when in the open conformation; d) the interaction of proximate label moieties in the closed conformation, preferably the quenching of a luminescent moiety by a quenching moiety; and e) the action of label moieties in the open conformation, preferably the ability of a luminescent moiety to luminescence when stimulated by light of an appropriate frequency. Such surfaces are known in the art.

Probes of this invention may be tethered by numerous molecular linking moieties 102 known to those skilled in the art. For example, a suitable linking moiety 102 comprises an alkyl chain or an oligonucleotide chain (such as oligouridine). We prefer oligonucleotide linking moieties because they are easily incorporated into probes. As persons skilled in the art will appreciate, the nucleotide sequence of such an oligonucleotide linking moiety should not be substantially complementary to any other sequence in the probe.

Tethered probes according to this invention are advantageously useful in assays for the simultaneous determination of a predetermined set of target sequences. For example, a series of luminescent probes can be prepared, each comprising a different target complement sequence. Each probe may be linked to the same support surface, such as a dipstick, at its own predetermined location. After contacting the support and the sample under hybridization conditions, the support may be stimulated with light of an appropriate frequency. Luminescence will occur at those locations where tethered probes have formed hybrids with target molecules from the sample. If the tethered probes are allele-discriminating probes, a single assay can determine which mutations or alleles of a particular gene are present, for example.

Such assays are particularly useful in clinical situations, e.g., in which a patient has an obvious infection, and the physician needs to know the identity of the infectious agent in order to prescribe effective treatment rapidly.

Assay kits according to this invention include at least one probe of this invention and instructions for performing an assay. Kits may also include assay reagents, e.g., salts, buffers, nuclease inhibitors, restriction enzymes and denaturants. Kits may include a target or model target for a positive control test, and a target-less "sample" for a negative control test.

Amplification assay kits may include, in addition to some or all of the above, primers, nucleotides, polymerases and polymerase templates for the assay and for control assays.

Vital stain kits may include, in addition to probe and instructions, permeabilizing agents, liposome precursors, buffers, salts, counterstains and optical filters.

In situ kits may include, in addition to probe and instructions, fixatives, dehydrating agents, proteases, counterstains, detergents, optical filters and coated microscope slides.

Kits may include probes which are allele-discriminating probes. Such kits are useful in ascertaining the allelic status of an organism and to discriminate between closely related organisms. Allele-discriminating probe kits with non-interactively labeled probes may include capture probes and magnetic beads for use in separation of bound probes from unbound probes. Where appropriate to the chosen label, a kit may include detection reagents.

Field kits may include, in addition to instructions, tethered probes with interactive labels according to this invention. At least one probe may be tethered to beads, wells or a dipstick. Multiple probes may be included, including a positive control probe that will hybridize to a component of uninfected samples.

Field kits may include, in addition to instructions, tethered probes according to this invention. Such kits may be for infectious agents or genes. Kits for genes may include negative and, sometimes, positive targets.

Probe constructs may be tested to determine whether they are unitary probes of the present invention under particular assay conditions. A test may be designed which is appropriate to the affinity pair and label moieties used in the probe construct.

For example, when a probe has interactive labels the test should be conducted under the conditions of the hybridization assay, using the detector to be used, and generally comprises the following steps: first, one measures the level of signal that is generated in the absence of target, then one measures the level of signal that is generated when there is an excess of probes in the presence of the minimum level of target which one needs to detect. If the level of signal from the first measurement is in accord with the level expected from proximate label moieties, if the level of signal from the second measurement is in accord with the level expected due to opening of the probes, and if the detector can reliably distinguish between the levels of signal from the two measurements, the construct is a probe according to this invention in that assay.

If the probe construct has oligonucleotide arms as the affinity pair, the probe construct must pass the test described in Example V to be a probe according to this invention.

To determine whether or not a probe with non-interactive labels is an allele-discriminating probe according to this invention, it must be determined whether or not that probe, under the assay conditions to be used, forms a stem duplex in the absence of its target sequence and shifts to the open conformation by hybridizing to its target sequence. This can be done by making a variant of the probe in which the interactive label pair DABCYL and EDANS are substituted for the intended non-interactive label, and submitting the variant, under the intended assay conditions, to the test described in Example V. For radioactively labeled Probe F, described below, we did this by testing Probe D, which has the same nucleotide sequence but interactive labels. Often, it will be possible to add DABCYL and EDANS to the non-interactively labeled probe in question, rather than substituting the pair for the non-interactive label.

To determine whether or not a probe according to this invention with interactive labels is an allele-discriminating probe, the probe is further tested against non-targets having an internally located mismatch. If the level of signal detected in a test assay using perfectly complementary target is at least five times higher above background than signal above background in a test assay using a non-target with a single internally located mismatch, the probe is an allele-discriminating probe according to this invention under the assay conditions. We prefer, however, that this ratio be even higher, preferably at least ten times higher or more preferably at least twenty times higher.

To determine whether or not a probe with non-interactive labels that passed the initial test described above is an allele-discriminating probe according to this invention, the probe is further tested in common heterogeneous assays against perfect target sequences and non-targets having an internally located mismatch. If the level of non-interactive signal detected in a test assay using perfectly complementary target is at least three times higher above background than non-interactive signal above background in an identical test assay using a non-target with a single mismatch, the probe is an allele-discriminating probe according to this invention under the assay conditions. We prefer, however, that this ratio be even higher, preferably at least five times higher, more preferably at least ten times higher and most preferably at least twenty times higher.

The following Examples illustrate several embodiments of the invention. They are not intended to restrict the invention, which is not limited to these specific embodiments.

EXAMPLE I

Synthesis of Probe A

Figure 3:
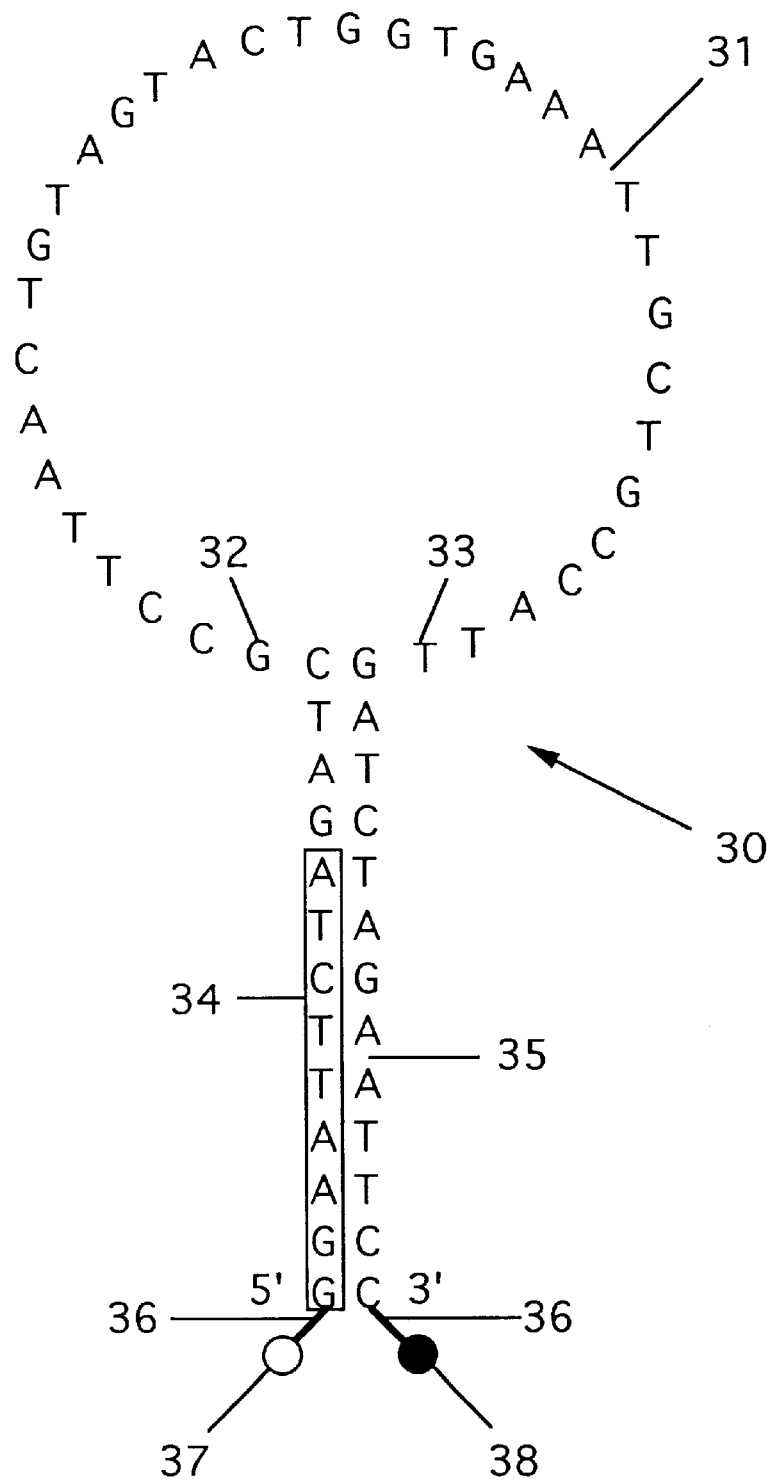
FIG. 3 is a schematic representation of Probe A of Example I, one of our most preferred unimolecular probes having interactive labels.

Probe A is depicted in FIG. 3. FIG. 3 shows the nucleotide sequence of a unimolecular probe 30 comprising target complement sequence 31 and complementary arms. The particular probe depicted in FIG. 3 is for detection of the integrase gene of the human immunodeficiency virus HIV-1 (Muesing et al., 1985). Target complement sequence 31, extending, 5' to 3', from nucleotide 32 to nucleotide 33 is complementary to the 35-nucleotide long target sequence 5'-AATGGCAGCAATTTCACCAGTACTACAGTTAAG GC-3'. It will be appreciated that a target complement sequence of the same length, complementary to another target, could be substituted. Probe 30 was assembled using the first two-oligonucleotide ligation method described above. Each of the two oligonucleotides 34, 35 were prepared by solid-state synthesis. During the synthesis of oligodeoxynucleotide 34, identified by a box in FIG. 3, a modified nucleotide was introduced at the 5' terminus. This nucleotide comprises a sulfhydryl group covalently bonded to the 5' phosphate via a hexa-alkyl spacer. Oligonucleotide 34 was then coupled to the EDANS label moiety 37. The method of Connoly and Rider (1985), incorporated herein by reference, was used to couple a sulfhydryl-reactive form of EDANS (1,5-IAEDANS, Molecular Probes, Eugene, Oreg.) to the oligonucleotide via a thioether bond. Oligonucleotide 34 was then purified by high-pressure liquid chromatography (HPLC). During the synthesis of oligonucleotide 35, the method of Nelson et al., (1989), which is incorporated herein by reference, was used to introduce a primary amino group covalently attached via a hepta-alkyl spacer to the 3' oxygen of the 3'-terminal nucleotide. About 2.5 mg of oligonucleotide 35 was kinased at its 5' end with $^{32}P$ using T4 polynucleotide kinase. The $^{32}P$ was used to trace the oligonucleotide during synthesis and purification. Kinased oligonucleotide 35 was then dissolved in 300 µl of 0.2 M sodium bicarbonate and reacted with 300 µl 60 mg/ml of the amino-reactive form of label moiety 38, DABCYL succinimidyl ester (Molecular Probes, Eugene, Oreg.). The amino-reactive DABCYL was added to a continuously stirred reaction mixture in fifteen aliquots of 20 µl each, over a 72-hour period. The reaction mixture was then precipitated with ethyl alcohol by adding ammonium acetate followed by ethyl alcohol. Oligonucleotide 35 was then purified by HPLC. Oligonucleotides 34 and 35 were then annealed to each other and ligated by incubation with T4 DNA ligase, at 16° C. The ligated product was purified by polyacrylamide gel electrophoresis in the presence of 7 M urea. The band containing Probe A showed blue-white fluorescence in the presence of urea (due to the EDANS), was orange in color (due to the DABCYL), and was radioactive (due to the $^{32}P$) Purified Probe A was eluted from the gel and was stored in 10 mM Tris-HCl, pH 8.0 containing 1 mM EDTA (TE buffer).

EXAMPLE II

Universal Stem and a Method of Using Same

Figure 4:
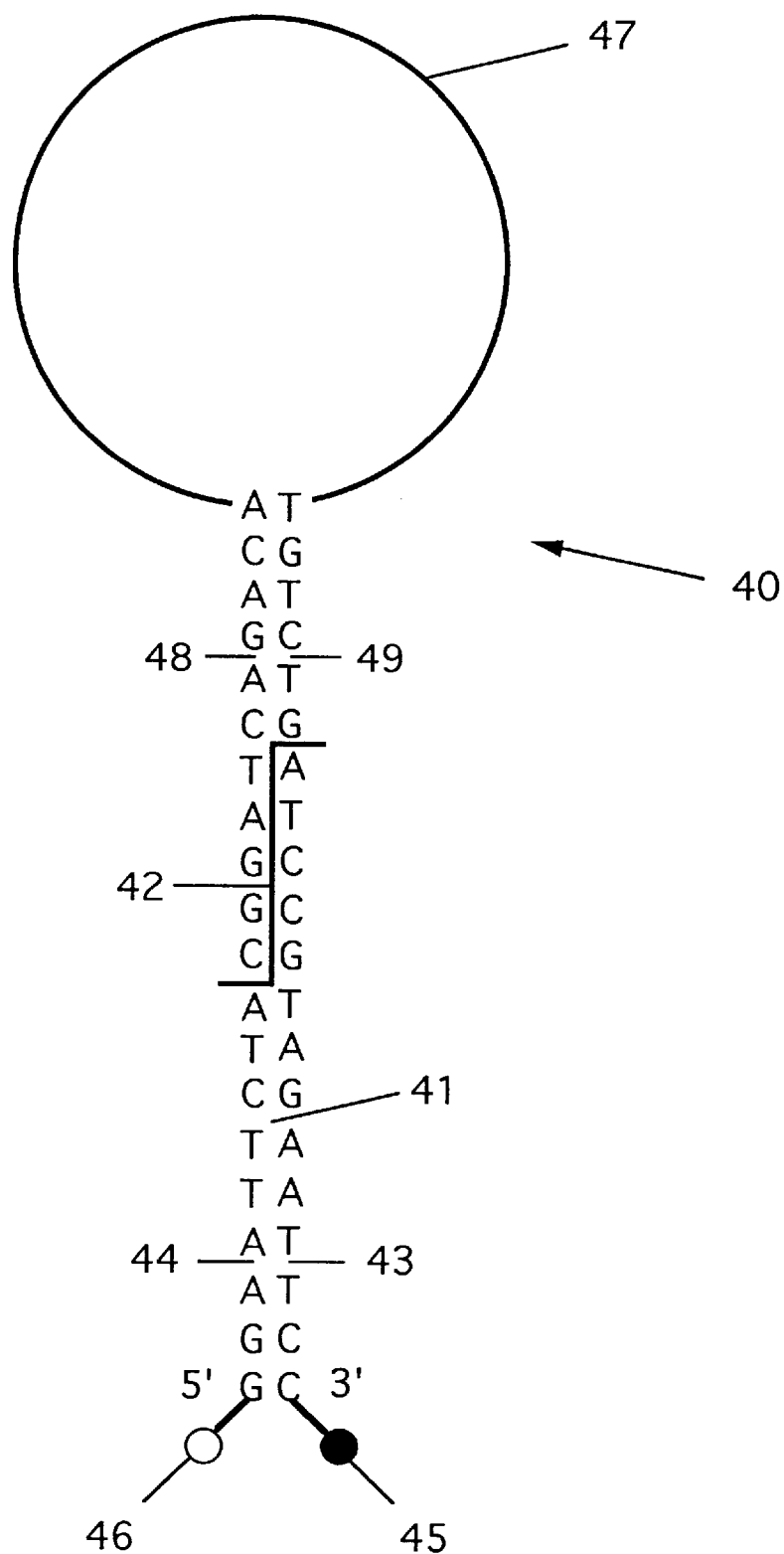
FIG. 4 is a schematic representation of the use of a universal stem having interactive labels as in Example II.

FIG. 4 shows probe 40, also referred to herein as Probe B, designed using a universal stem according to this invention. Referring to FIG. 4, universal stem 41, delineated by line 42 for clarity, comprises arm regions 43, 44, to which may be ligated a strand containing any target complement sequence, as described below.

To assemble universal stem 41, two oligonucleotides 43, 44 were produced by solid-state synthesis. Oligonucleotide 43 was kinased using T4 polynucleotide kinase. Oligonucleotides 43, 44 are complementary. One, in this case oligonucleotide 43, is 5 nucleotides longer than the other, oligonucleotide 44. Referring to FIG. 4, those five nucleotides are 5'-ATCCG. Oligonucleotide 43 was conjugated to label moiety 45, a DABCYL moiety, at its 3' terminus. Oligonucleotide 44 was conjugated to label moiety 46, an EDANS moiety, at its 5' terminus. These conjugations were performed and the conjugated oligonucleotides were purified as described in Example I. Oligonucleotides 43, 44 were then annealed, thereby placing label moieties 45, 46 in close proximity to each other.

Oligonucleotide 47, prepared by solid-state synthesis, includes a target complement sequence, depicted as a line in FIG. 4, flanked by regions comprising the remaining portions 48, 49 of the arm sequences. Arm portions 48, 49 were annealed to each other to form an overhang complementary to the overhang on the universal stem. The overhang, 5'-CGGAT, comprises the first five nucleotides of arm portion 48. Oligonucleotide 47 was then annealed to universal stem 41 and ligated to it, under the conditions of Example I. Probe B was isolated from the ligation mixture by gel electrophoresis. Although stem sequences 43, 44 and arm portions 48, 49 were annealed separately prior to being mixed, they could have been annealed after mixing. The final arm stem of probe 40 comprises the combination of regions 44 and 48 and regions 43 and 49, respectively.

EXAMPLE III

Synthesis of Probe C

Figure 5:
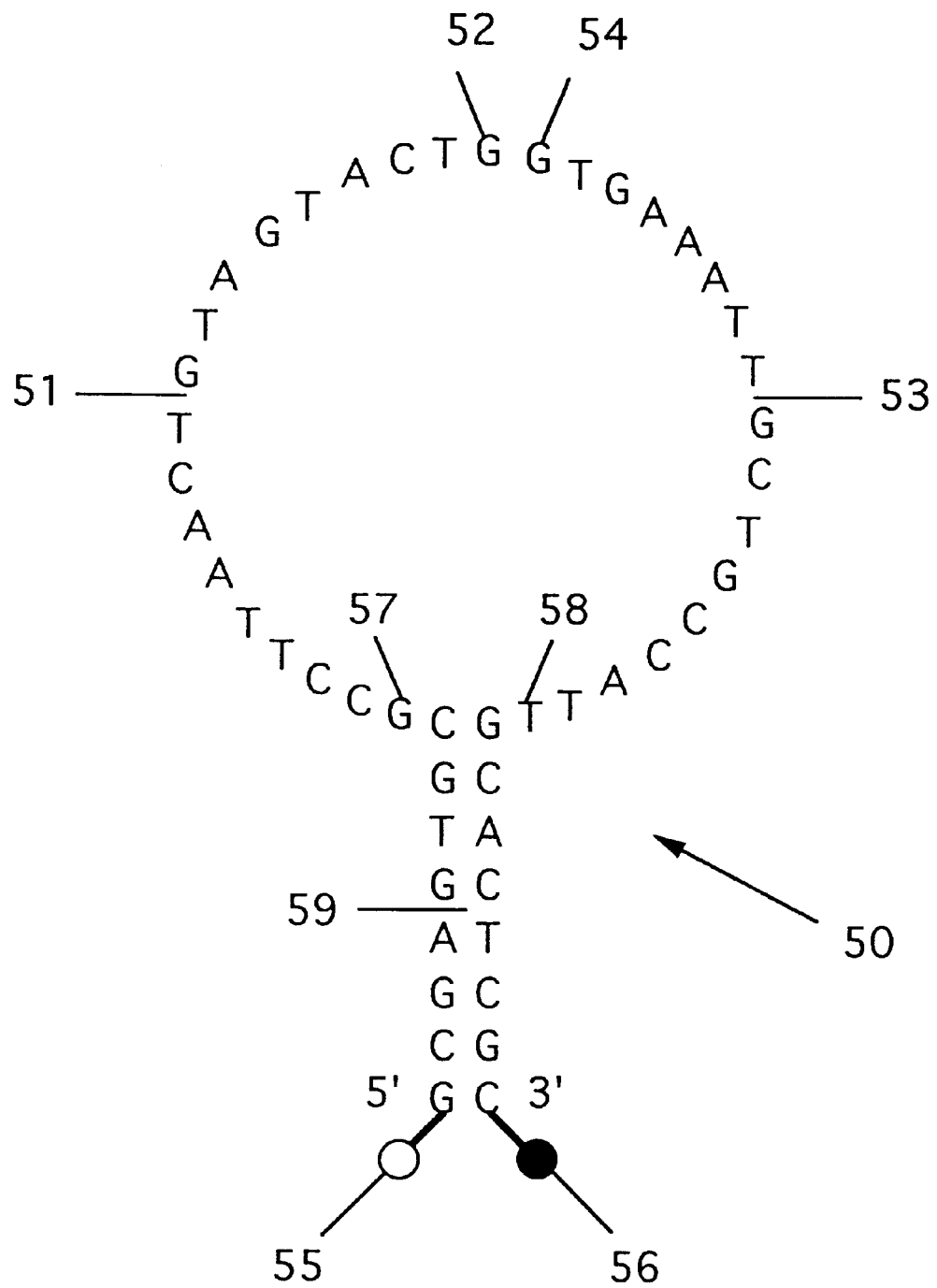
FIG. 5 is a schematic representation of the unimolecular Probe C of Example III.

Probe C, a unimolecular probe depicted in FIG. 5, was constructed by the second two-oligonucleotide method described above. Oligonucleotide 51, extending from the 5' end of probe 50 to nucleotide 52, and oligonucleotide 53, extending from nucleotide 54 to the 3' terminus of probe 50 were prepared by solid-state synthesis. Oligonucleotide 51 was conjugated to EDANS 55 at its 5' terminus and oligonucleotide 53 was conjugated to DABCYL 56 at its 3' terminus. The conjugations and purification of the conjugated oligonucleotides were performed as described in Example I.

At this point, the two molecules, oligonucleotides 51 and 53 can be annealed to form a bimolecular probe of this invention. A unimolecular probe was formed from these oligonucleotides by annealing them to an oligonucleotide splint having the sequence 5'-AATGGCAGCAATTTCACC AGTACTACAGTTAAGGC-3' and ligated at the junction of nucleotides 52 and 54. The unimolecular probe was then electrophoretically purified as described in Example I. Probe C has the same target complement sequence as Probe A but was designed for use under different conditions. The target complement sequence extends, 5' to 3', from nucleotide 57 to nucleotide 58. The stem duplex 59 of probe C is eight base pairs long.

EXAMPLE IV

Synthesis of Probe D and Probe E

Oligodeoxynucleotides that contain a protected sulfhydryl group at their 5' end and a primary amino group at their 3' end were purchased from the Midland Certified Reagent Company. In these oligodeoxynucleotides the sulfhydryl group was connected to the 5' phosphate via a —$(CH_2)_6$— spacer and the primary amino group was linked to the 3' hydroxyl group via a —$(CH_2)_7$— spacer. The first coupling reaction links a DABCYL moiety to each 3'-amino group. For each oligonucleotide a 500 µl solution containing 0.6 mM oligodeoxynucleotide and 0.1 M sodium bicarbonate was reacted with a 500 µl solution of 60 mg/ml of the succinimidyl ester of DABCYL (Molecular Probes, Eugene, Oreg.); dissolved in N,N-dimethyl formamide. The succinimidyl ester of DABCYL was then added in small aliquots to a continuously stirred reaction mixture at room temperature over a 72 hour period. The oligonucleotide in this reaction mixture was then precipitated by the addition of 300 µl of 3 M sodium acetate, 1.7 ml water and 7.5 ml ethanol in order to remove the excess dye.

The second coupling reaction linked EDANS to the 5'-sulfhydryl group. Just before coupling the oligonucleotide with EDANS, the S-trityl protective group was removed from the 5' end of the oligodeoxynucleotide. The precipitated oligonucleotide was dissolved in 1 ml of 0.1 M triethylamine (pH 6.5). This solution was treated with 10 µl of 0.15 M silver nitrate (a 5-fold molar excess of silver nitrate) for 30 minutes at room temperature. Fourteen µl of 0.15 M dithiothreitol (7-fold excess of dithiothreitol) was then added to this mixture. After a 5-minute incubation at room temperature, a precipitate was formed which was removed by centrifugation. The modified oligonucleotide in the supernatant was then treated with a 500 µl of 3M 1,5 IAEDANS (Molecular Probes, Eugene, Oreg.) dissolved in 0.2 M sodium bicarbonate (a 5-fold molar excess of the sulfhydryl-reactive form of EDANS) for one hour at room temperature (Connolly and Rider 1985, herein incorporated by reference). The modified oligonucleotide was then precipitated by the addition of ammonium acetate and ethanol. The oligodeoxynucleotide containing both EDANS and DABCYL was purified by high pressure liquid chromatography (Beckman) as follows: The precipitated oligonucleotide was dissolved in 1 ml of triethylammonium acetate (pH 6.5). This mixture was fractionated on a C-18 reverse phase column (Nucleogen DEAE 60-7), using a linear gradient of 0–75% Acetonitrile containing 0.1 M triethylammonium acetate (pH 6.5), run for 40 minutes at a flow rate of 1 ml/min. The fractions that absorbed at 260 and 336 nm and that exhibited fluorescent emission at 490 nm were isolated. These fractions had the characteristic fluorescence of EDANS and exhibited the melting thermal denaturation profile discussed below.

The sequence of Probe D was EDANS-5'-GCGAGAAGTTAAGACCTATG<u>CTCGC</u>-3'-DABCYL and of Probe E was EDANS-5' <u>GCGAGTG</u> CGCCTTAACTGTAGTACTGGTGAAATTG CTGCCATT<u>GCACTCGC</u>-3'-DABCYL, where in each case the underlined segments are the arms, which participate in the formation of the stem, and the intervening sequence constitutes the target complement sequence. Probe E had the same nucleotide sequence as Probe C (FIG. 5).

EXAMPLE V

Testing Probe Constructs

This example describes the test to determine whether or not a probe constructed with nucleic acid arm sequences is a probe according to this invention under particular assay conditions. Data for one such probe construct, Probe A, is provided and evaluated. Probe A was found to be a probe of this invention in an assay at 20° C. without any salt.

Figure 6:
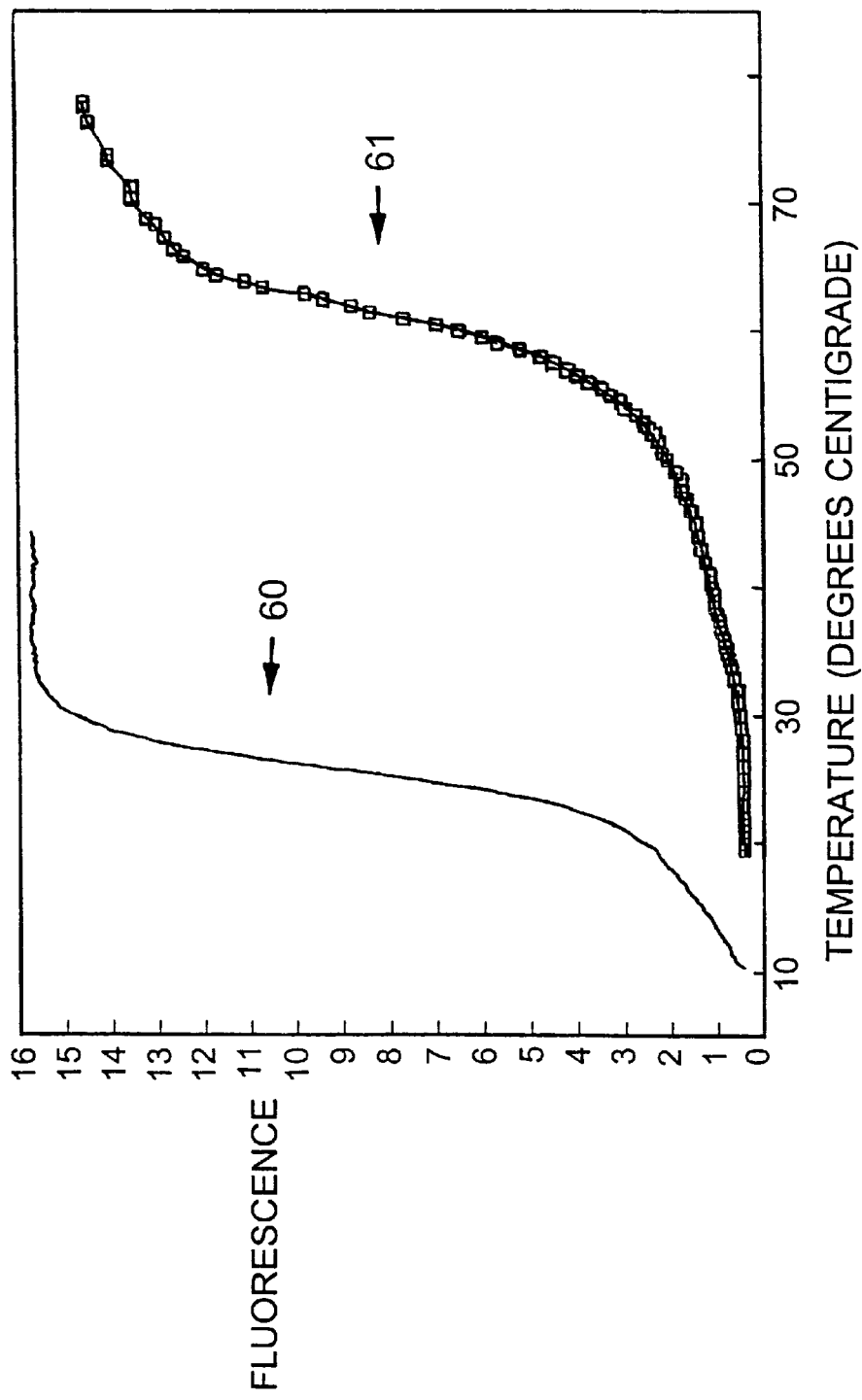
FIG. 6 depicts the thermal denaturation curves of Probe A and Probe C according to Example V.

Probes of this invention exhibit a characteristic melting temperature, Tm, the temperature at which two hybridized nucleic acid strands separate due to thermal energy. The melting temperature of Probe A was determined by monitoring the level of its fluorescent signal as temperature was increased from 10° C. to 80° C. under preselected assay conditions: TE buffer with no added salt. The concentration of probes was 150 pmoles in a volume of 2 ml TE buffer. Thermal denaturation or transition curves were recorded with a Perkin-Elmer LS-5B fluorometer. The EDANS moiety of Probe A was excited at 336 nm, and the level of fluorescence at 490 nm was monitored. The results are shown in FIG. 6. Instrumental tracing 60 represents the thermal denaturation curve of Probe A under these assay conditions. The Tm of a probe is indicated by the inflection point of its thermal denaturation curve. The melting temperature, Tm, of Probe A was 27° C.

The following levels of signal, here fluorescence, are noted from the thermal denaturation curve: a first level at Tm−10° C., a second level at Tm+10° C., and a third level at the detection temperature of the preselected assay. A probe construct is a probe of this invention under the preselected assay conditions if under those conditions at the detection temperature, addition of excess of model target results in a change in the signal level in the direction toward the level at Tm+10° C. by an amount equal to at least ten percent of the difference between the signal levels at Tm−10° C. and Tm+10° C. "Model target" is a nucleic acid strand containing a sequence complementary to the target complement sequence of the probe construct and no more than one additional nucleotide immediately adjacent, 5' or 3', thereto. Often, actual target will meet this definition. The concentration of probe constructs used to measure the signal level in the presence of model target is the same concentration used to measure the signal levels in the absence of target, i.e., the concentration used to obtain the thermal denaturation curve.

For Probe A, signal levels were determined from instrumental tracing 60 presented in FIG. 6, as follows: at Tm−10° C., a level of 2 units; at Tm+10° C., a level of 16 units; and at the detection temperature, 20° C., a level of 2.5 units. Addition of excess target at the detection temperature shifted the level from 2.5 units to 14.5 units in 3 hours using a large excess of model target, as described below. Thus, Probe A is a probe of this invention under these preselected assay conditions.

Figure 8:
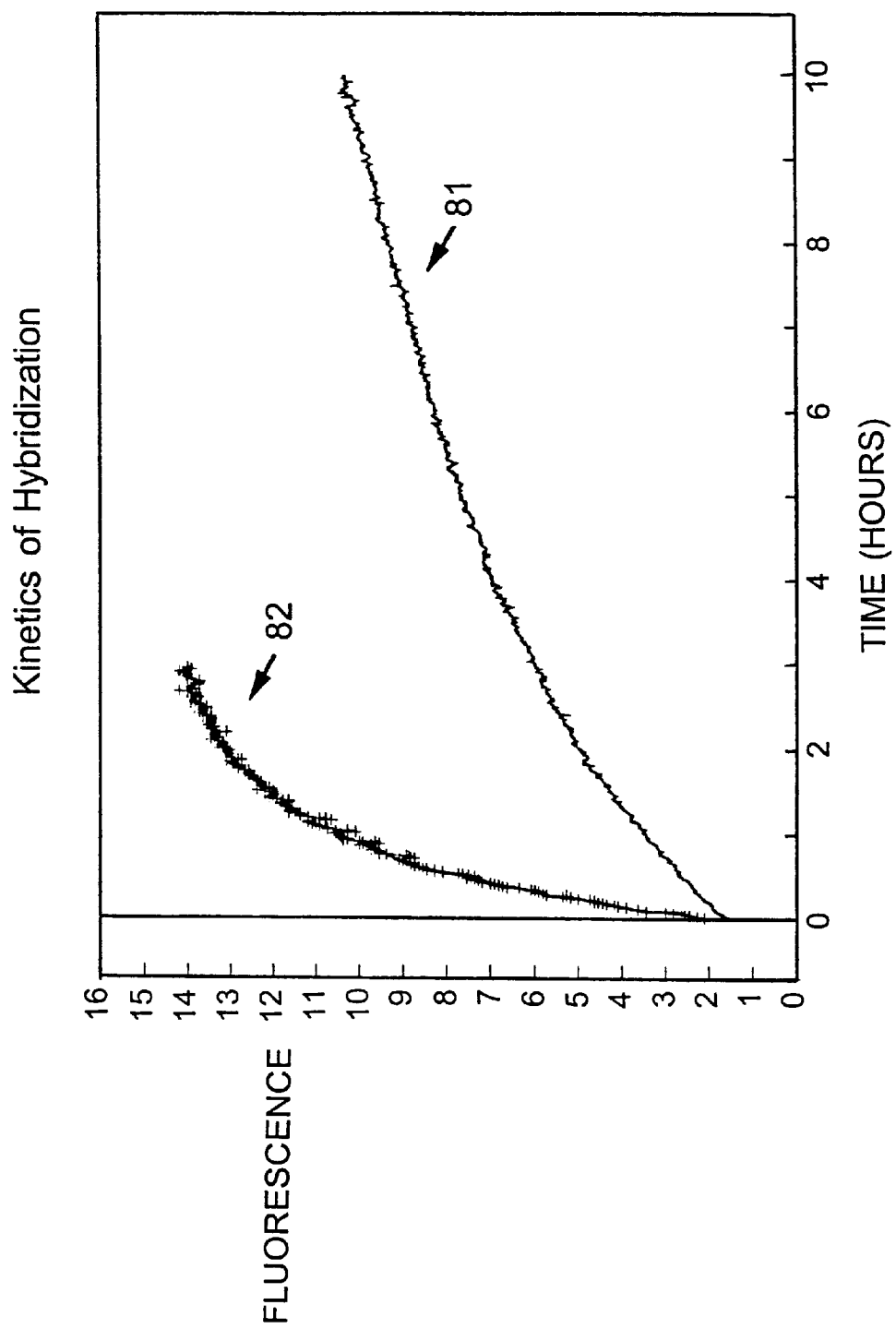
FIG. 8 is a graph of the kinetics of hybridization of Probe A according to Example V.

The model target was a DNA strand having the sequence: 5'-CAGAC AATGGCAGCAATTTCACCAGTACTACAGTTAAGGCC GCCTGT-3' which was produced by solid-state synthesis and purified by HPLC. The underlined subsequence identifies the 35-nucleotide long target sequence for Probe A. Model target, 25 nmoles, was added to 2 ml TE buffer containing 150 pmoles of Probe A. Fluorescence was monitored over time in a Perkin-Elmer LS-5B fluorometer with a quartz cuvette maintained at the detection temperature. Instrumental tracing 82 in FIG. 8 shows the results. FIG. 8 shows that a high rate of change of fluorescence occurred early, diminished over time and approached a plateau. The test point is the plateau level, although, as in this case, one need not wait that long if a "test passing" level is achieved earlier. As will be recognized, the time to the plateau level depends on the concentration of model target. For example, when we reduced the model target concentration five-fold, instrumental tracing 81 in FIG. 8, the plateau was not reached even after ten hours.

Another construct, Probe C, was tested under different preselected assay conditions, 10 mM $MgCl_2$ in TE buffer at 37° C. Its thermal denaturation curve, instrumental tracing 61 in FIG. 6, gives its Tm as 61° C. From the data in instrumental tracing 61, and from measurement of signal in the presence of excess model target at 37° C., Probe C was found to be a probe according to this invention under the preselected assay conditions. A bimolecular embodiment of unitary Probe C was tested under the same assay conditions used to test the unimolecular embodiment of unitary Probe C. The bimolecular probe was also found to be a probe of the present invention. Bimolecular probes exhibit virtually the same hybridization kinetics as their unimolecular counterparts.

Thermal denaturation profiles and all other fluorescence measurements for experiments with Probe D and Probe E were performed on an LS-5B spectrofluorometer (Perkin-Elmer) using a QS cell (Hellma Cells New York) whose temperature was controlled by a circulating bath. The probes were excited at 336 nm and the fluorescence emission was measured at 490 nm.

Figure 11:
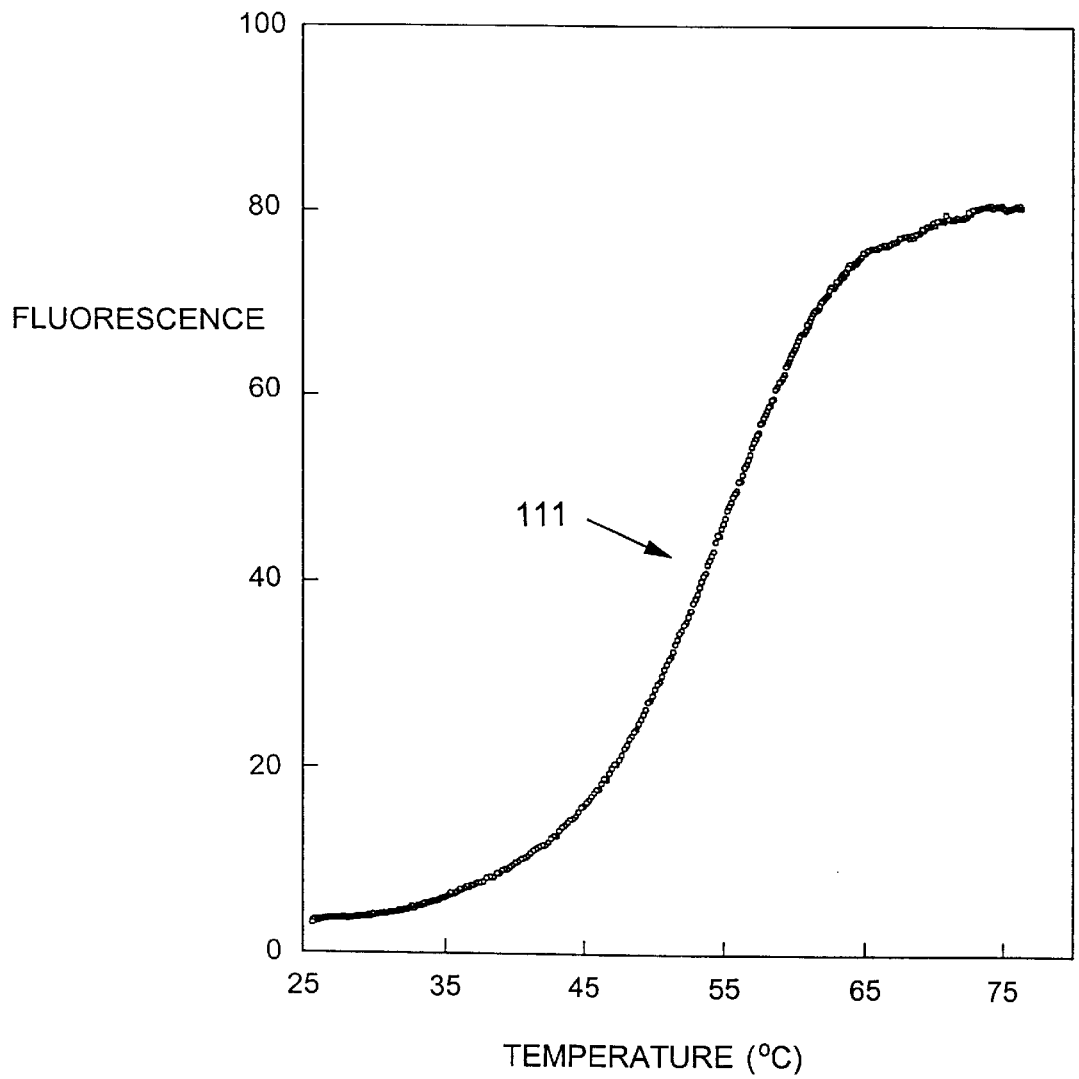
FIG. 11 depicts the thermal denaturation curve of Probe D according to Example V.

The fluorescence of a 150 microliter solution (170 nM Probe D, 100 mM Tris-HCl, 1.0 mM $MgCl_2$ pH 8.0) was monitored as the temperature was changed from 25° C. to 75° C. at a rate of 2° C./min. The thermal denaturation profile is shown in FIG. 11 (curve 111). When the temperature of a solution containing the probe was increased, its fluorescence changed in a manner which is characteristic of the melting of a nucleic acid double helix. The display of a distinct thermal transition indicates that at a low temperatures the arms formed a stem duplex and at high temperatures the helical order of the stem melted, and the probe assumed a random-coil configuration. The melting temperature of robes according to this invention depend upon the length and the guanosine-cytosine content of the arm sequences and the concentration of Mg and other salts in the medium. Compare, for example, the melting behavior (FIG. 6) of Probes A and C, which have 35-nucleotide long target complement sequences but different arms and different test assay conditions. Divalent cations have a particularly powerful influence upon the melting temperature. For example, the melting temperature of Probe A (FIG. 3), was 27° C. in the absence of magnesium ions, but was 56° C. in the presence of as little as 1 nM $MgCl_2$. Probes according to this invention with even shorter (eight or five nucleotide-long) arms were found to exist as random coils in the absence of magnesium ions. They formed stable stem duplexes in presence of as little as 1 mM $MgCl_2$.

From the levels of fluorescence at 25° C. and 75° C. in FIG. 11 (curve 111), it is estimated that the fluorescence of EDANS in Probe D is quenched by 96 percent when the probe has a stem duplex and by 19 percent when the probe is in the state of a random coil. The vertical axis in FIG. 11 is a linear scale of fluorescence ranging from 0 to 100. The minimum limit of the scale is set by the level of fluorescence of the buffer solution (100 mM Tris-HCl and 1 mM $MgCl_2$ pH 8.0), and the maximum limit is set by the fluorescence of a 170 nM solution of Probe D bound to its target sequence. We have shown that when the arms form a stem duplex, the degree of quenching does not depend on the length of the probe. In the random coil state, however, smaller probes according to this invention were quenched to a larger extent than longer ones. For example, a 51-nucleotide long probe, Probe E, displayed as much fluorescence upon melting as it did upon binding to its target.

Figure 12:
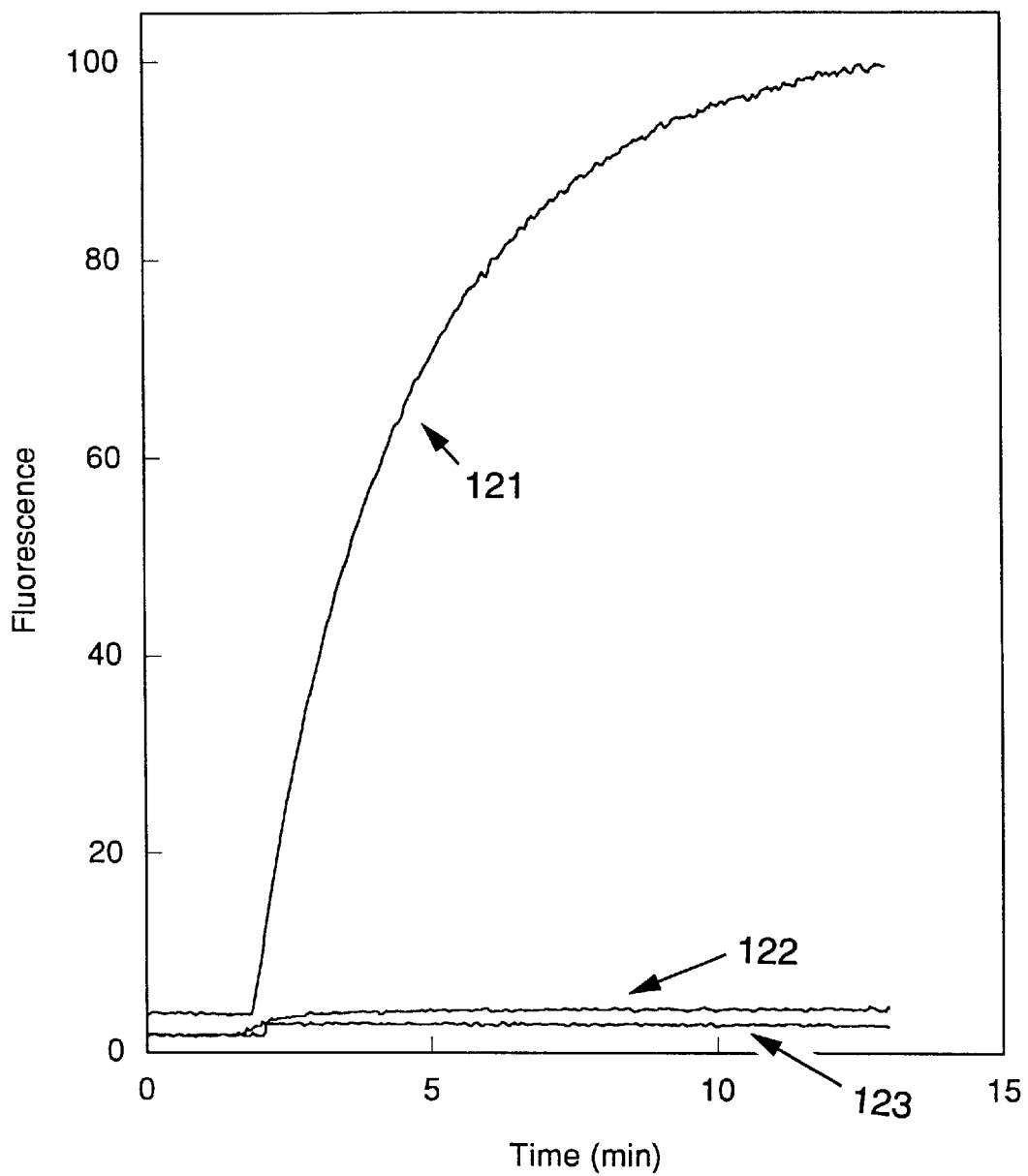
FIG. 12 is a graph of the kinetics of hybridization of Probe D, an interactively labeled allele-discriminating probe according to this invention.

Probe D has been determined to be a probe according to this invention under the described assay conditions by comparing its thermal denaturation curve (FIG. 11, curve 111) with its hybridization curve 121 (FIG. 12). In order to obtain the hybridization curve 121 for Probe D, the solution of Probe D specified above was first maintained at 25° C., and fluorescence was monitored. After confirming that the level of fluorescence was constant over the first two minutes, 5 µl of a 2.25 µM solution containing a model target oligodeoxynucleotide (5'-CATAGGTCTTAACTT-3') were added. There was a 5-fold molar excess of model target compared to the concentration of the probe. The level of fluorescence was recorded every second. The experiment was repeated with oligodeoxynucleotides that included a single internal nucleotide mismatch (5'-CATAGGT GTTAACTT-3') (curve 122 in FIG. 12), and a single internal nucleotide deletion (5'CATAGGT-TTAACTT-3') (curve 123 in FIG. 12). The identities of the mismatch and the deletion are indicated with an underline and hyphen, respectively.

As shown by curve 121 (FIG. 12), when a fully complementary single-stranded oligodeoxynucleotide model target was added to a solution of Probe D maintained at a temperature below its melting zone, the fluorescence of the solution increased dramatically over a short time. This increase was due to hybridization between the model target and the target complement sequence of the probe. The increase in fluorescence over time exhibited the characteristic second order kinetics of a hybridization reaction, i.e., the second order rate constant increased with increasing concentrations of the probe, target, salt or temperature. We prefer interactive labels comprising fluorophores and quenchers, because the signal-to-background ratio can be very large. FIG. 12 demonstrates that the ratio for Probe D under these conditions was 25:1 where EDANS and DABCYL were the label pair. A similar increase in fluorescence was observed when an RNA target was used. When such RNA-DNA hybrids were treated with ribonuclease H, the fluorescence returned to its lowest level, due to digestion of the RNA in the RNA-DNA hybrid.

The increase in fluorescence due to hybridization of Probe D to its target is greater than the increase in fluorescence due to the thermal denaturation of its stem. This can be seen by comparing FIGS. 11 and 12, whose vertical axes are identical in scale. We theorize that this difference is observed because in the random coil conformation assumed by melted Probe D, (which is only 25 nucleotides long) some quenching occurs, whereas when Probe D is hybridized to its target, the probe-target hybrid assumes a conformation in which quenching is reduced or does not occur.

In an additional experiment, the hybridization of Probe D was visualized without the aid of an instrument. Two tubes were prepared, each containing 10 µl of 16.4 micromolar Probe D, 100 mM Tris-HCl, 1 mM $MgCl_2$. To one tube, 1.5 µl of a 250 micromolar solution of the fully complementary model target was added. The fluorescence of that tube at room temperature was visible to the naked eye when both tubes were illuminated with a broadwavelength ultraviolet light source (Transilluminator, Model No. 3-3100, Fotodyne, New Berlin, Wis.). The other tube had virtually no fluorescence. The fluorescent signal appeared virtually instantaneously. The tubes were successfully photographed without filters using Kodak Ektachrome ASA 200 film and an exposure time of 0.25 second.

EXAMPLE VI

Demonstration of Probe Function

Additional tests with Probe A were run to demonstrate probe function. Probe A was tested with an excess of DNA target and with an excess of RNA target. The DNA target was the model target described in Example V above. The RNA target was an 880-nucleotide RNA corresponding to the integrase gene of HIV-1 (Muesing et al., 1985). The sequence of the DNA model target is contained within the sequence of the RNA target.

The target nucleic acids and Probe A were suspended in TE buffer. Five 0.5 ml plastic snap-capped tubes were prepared containing: 1) 1,000 pmoles of DNA target; 2) 80 pmoles of RNA target; 3) 80 pmoles of RNA target and 15 pmoles of Probe A; 4) 1,000 pmoles of DNA target and 15 pmoles of Probe A; and 5) 15 pmoles of Probe A. The final volume of each test was adjusted to 6 µl with TE buffer.

Figure 7:
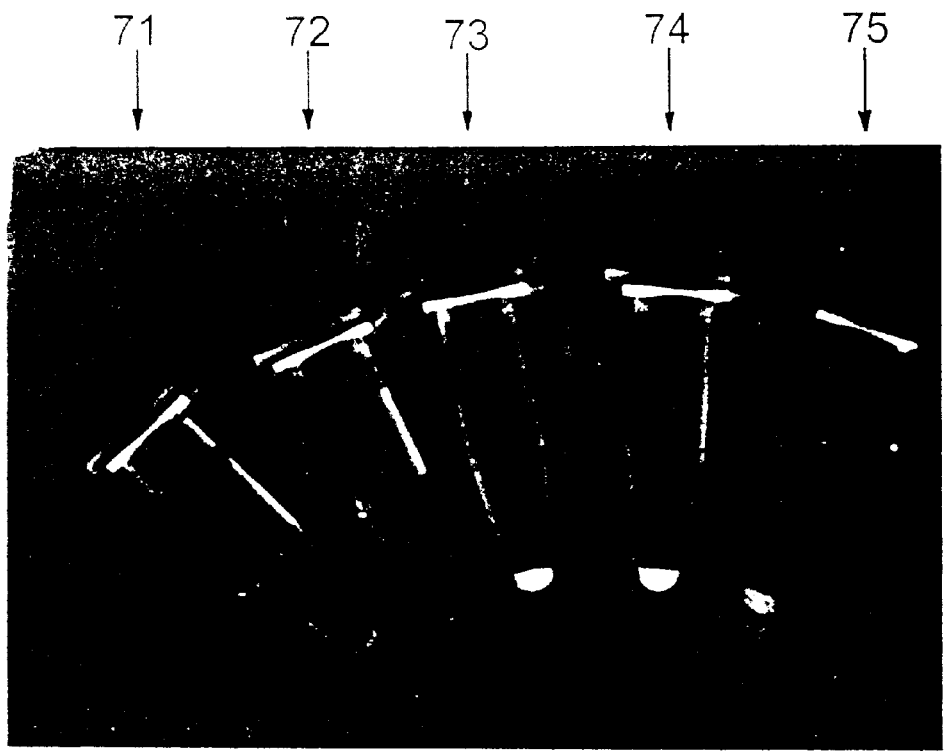
FIG. 7 is a photograph illustrating results of Example VI.

While illuminating the tubes with ultraviolet light from a Transilluminator (Model No. 3-3100, Fotodyne, New Berlin, Wis.) the tubes were mixed by gently pipetting twice with a Gilson micropipettor. Intense blue fluorescence, indicating detection of the targets by Probe A, was observed by eye and photographed. Results 71–75, corresponding to tubes 1–5, respectively, are shown in FIG. 7.

The appearance of a fluorescent signal was virtually instantaneous in the tube containing the DNA target and occurred in several minutes in the tube with the RNA target. The delay with the RNA target is believed due to the lower amount of target used, although it could be due to sequestering of the target sequence by the surrounding sequences in the RNA. In a control test, unrelated nucleic acids were mixed with Probe A. No fluorescence was observed in these controls (data not shown).

From the results of these experiments, we infer that: a) in the absence of target, well-designed probes of this invention have a very low level of background signal; b) probe-target hybridization can produce a signal change detectable by the human eye; c) probes of this invention work with either RNA or DNA targets; and d) in the presence of target, probes of this invention can turn "on" very rapidly, within a few seconds. Additionally, rapid heating and cooling of Probe A in the absence of target sequence demonstrated that the probe also turned "off" very rapidly, virtually instantaneously.

The sample used in the test reported in FIG. 8, tracing 82, was subsequently heated to 95° C., rapidly cooled in an ice bath, and incubated again at 20° C., the detection temperature. The kinetics of signal generation was followed as before. The tracing during incubation at 20° C. was virtually indistinguishable from tracing 82. This demonstrates that with well designed unimolecular probes of this invention having oligonucleotide arms as the affinity pair, probe-target hybrids are reversibly thermally denaturable. Thus, those embodiments are suitable for incorporation into thermal cycling reactions, such as PCR, for real-time detection of amplification products.

FIG. 12 demonstrates that Probe D is an "allele-discriminating probe" according to this invention under the assay conditions reported above. Curve 121 shows the large increase in fluorescence due to the hybridization of Probe D to its fully complementary model target. When an oligodeoxynucleotide that contained a single nucleotide mismatch in its center was added to a solution of Probe D, practically no increase in fluorescence was observed (curve 122). Similarly, addition of an oligonucleotide that contained a single nucleotide deletion lead to practically no increase in fluorescence (curve 123). The addition of unrelated nucleic acids also did not lead to any increase in fluorescence under the reported assay conditions.

Curve 121 demonstrates that Probe D recognized and bound to its fully complementary model target by hybridization of the target complement sequence to the preselected nucleic acid target sequence. Curves 122 and 123 prove that Probe D did not hybridize to minimally imperfectly matched oligonucleotides. Curves 122 and 123, in conjunction with curve 121, demonstrate that Probe D effectively discriminates between the fully complementary model target and oligonucleotides in which a single nucleotide was either changed or deleted. Because Probe D discriminates against the slightly mismatched oligonucleotides, we refrain from calling those oligonucleotides "model targets." Only perfectly complementary sequence and possibly sequences varying in hybridization energy by less than does a sequence with one internally located mismatch are targets for allele-discriminating probes according to this invention under appropriate assay conditions.

Thus, we have demonstrated that allele-discriminating probes can be designed so that a hybrid forms virtuallly only with a perfectly matched target sequence. If a probe with non-interacting label(s) is used, washing can be employed to separate "allele-discriminating probes" hybridized to an intended allele from probes not so hybridized.

EXAMPLE VII

Assays

Assays that utilize the probes of this invention begin simply by addition of the probes to the material of interest under conditions that are conducive to hybridization. The methods of processing the samples and monitoring the fluorescence signal may vary with the nature of the samples. Tissues may be disrupted mechanically or by incubation with chaotropic salts. Most disrupted tissues may be used directly in the assays. Some tissues, however, contain naturally fluorescent materials that may interfere with the detection of signal. In such cases, the nucleic acids may be isolated from the fluorescent materials either before or after hybridization. The fluorescence of opened probes can be monitored by fluorometers.

Preferred unitary probes of the present invention are useful in field tests for infectious diseases. For example, a test for malaria may begin by addition of guanidine thiocyanate to a sample of blood to lyse the cells, detoxify the cells and denature the constituents. A large excess of interactively labeled probe (relative to the expected maximal target concentration) which is complementary to the ribosomal RNA of the malarial parasite may then be added, and hybridization allowed to proceed. Fluorescence of open probes may be monitored either visually or with help of a fluorometer. Detection of a positive fluorescent signal indicates an infection by the malarial parasite.

Probes with interactive labels according to this invention can be used to locate particular nucleic acid fragments in a gel or other medium, for example where information on the size of a specific nucleic acid is desired. The nucleic acids in the sample can first be fractionated by gel electrophoresis and then the gel itself bathed in a solution containing the probes. The location in the gel where the target nucleic acid migrates will be detectable by the characteristic signal as a result of hybridization.

Probes with interactive labels of the present invention, preferably unimolecular, preferably having a fluorescer and quencher as the label moieties, can be used as vital stains for the detection of cells that harbor a target nucleic acid. Modified nucleotides are especially useful for such probes. In order to deliver the probes into the cells, a permeabilizing agent, such as toluene, is added to the tissue prior to the addition of the probes. Alternatively, probes can be encapsulated into liposomes and these liposomes fused with the cells. After the delivery of probes, hybridization takes place inside the cells. When the tissue is observed under a fluorescent microscope, the cells that contain the target nucleic acid will appear fluorescent. The subcellular location of a target nucleic acid can also be discerned in these experiments. Production of nucleic acids in synthesis reactions may be monitored by including appropriately designed probes with interactive labels in the reaction mixture and monitoring the level of signal, e.g., fluorescence, in real-time. The probes should be designed to be complementary to a segment of the nucleic acid that is produced. Examples of such reactions are RNA synthesis by DNA-dependent RNA polymerases and by Q-beta replicase. Unimolecular probes are particularly useful in tracking a polymerase chain reaction, since they open and close within a time period that is far shorter than the duration of an incubation step used in this reaction. An additional temperature in each cycle, which is 5–12° C. lower than the melting temperature of the stem of the probe, can be included as the detection temperature. In each cycle, the level of fluorescence will indicate the amount of target DNA strand present. An excess of the probes, as an excess of PCR primers, in the reaction mixture should be used. The PCR may be asymmetric. Real-time monitoring of the correct products, as opposed to end-point detection, improves the precision and the dynamic range of the estimates of the target nucleic acid concentrations by polymerase chain reactions and obviates the need for post-amplification analysis.

Probe E is an interactively labeled probe according to this invention under conditions typical for polymerase chain reactions. We used it to monitor the progress of a reaction. The target complement sequence of Probe E is complementary to the middle region of a 130-nucleotide-long target DNA fragment. This target is produced when primers 5'-CTCTTAAAATTAGCAGGAAG-3' and 5'-TGTAGGGAATGCCAAATTCC-3', and template plasmid that contained the integrase portion of the HIV-1 genome are used in a polymerase chain reaction.

The template plasmid was constructed as follows. A cDNA encoding a portion of the polymerase gene of HIV-1 strain NL4-3 (Adachi et al., (1986), listed in the Genbank database as HIVNL43) was subcloned between the Hind III and Xma I restriction sites in the polylinker of plasmid pGEM-4Z (Promega). The resulting plasmid, pGEM-Int, was used as template below.

Four series of polymerase chain reaction ("PCR") mixtures were prepared. The first series of reactions was initiated with one billion pGEM-Int template molecules. The second series of reactions was initiated with ten million template molecules. As controls, the third series had no template molecules, and the fourth series had template and primers chosen to produce an unrelated amplified product. Each PCR reaction (130 microliters) had 10 mM Tris-HCl, 1.5 mM $MgCl_2$, 50 mM KCl, 3.6 uM of each of the primers, 0.05 units/$\mu$l Taq DNA polymerase [Boehringer Mannheim: this preparation reportedly lacks 5' to 3' exonuclease activity; see Product Insert 1093. T 13.51.1180 975 MB GPM, citing Tindall, et al. 1988] and 0.27 $\mu$M Probe E. A temperature profile of 92° C. for 2 min, 55° C. for 3 min, and 72° C. for 3 min was repeated 35 times. Tubes containing reaction mixtures from each series were withdrawn from the thermal cycler (Coy Laboratories) after the completion of various numbers of cycles. At the end of the entire cycling program all reaction mixtures were heated to 92° C., cooled to 37° C., and their fluorescence was then measured. Curves 131–134 (FIG. 13) show these measurements from the first series through the fourth series, respectively.

Figure 13:
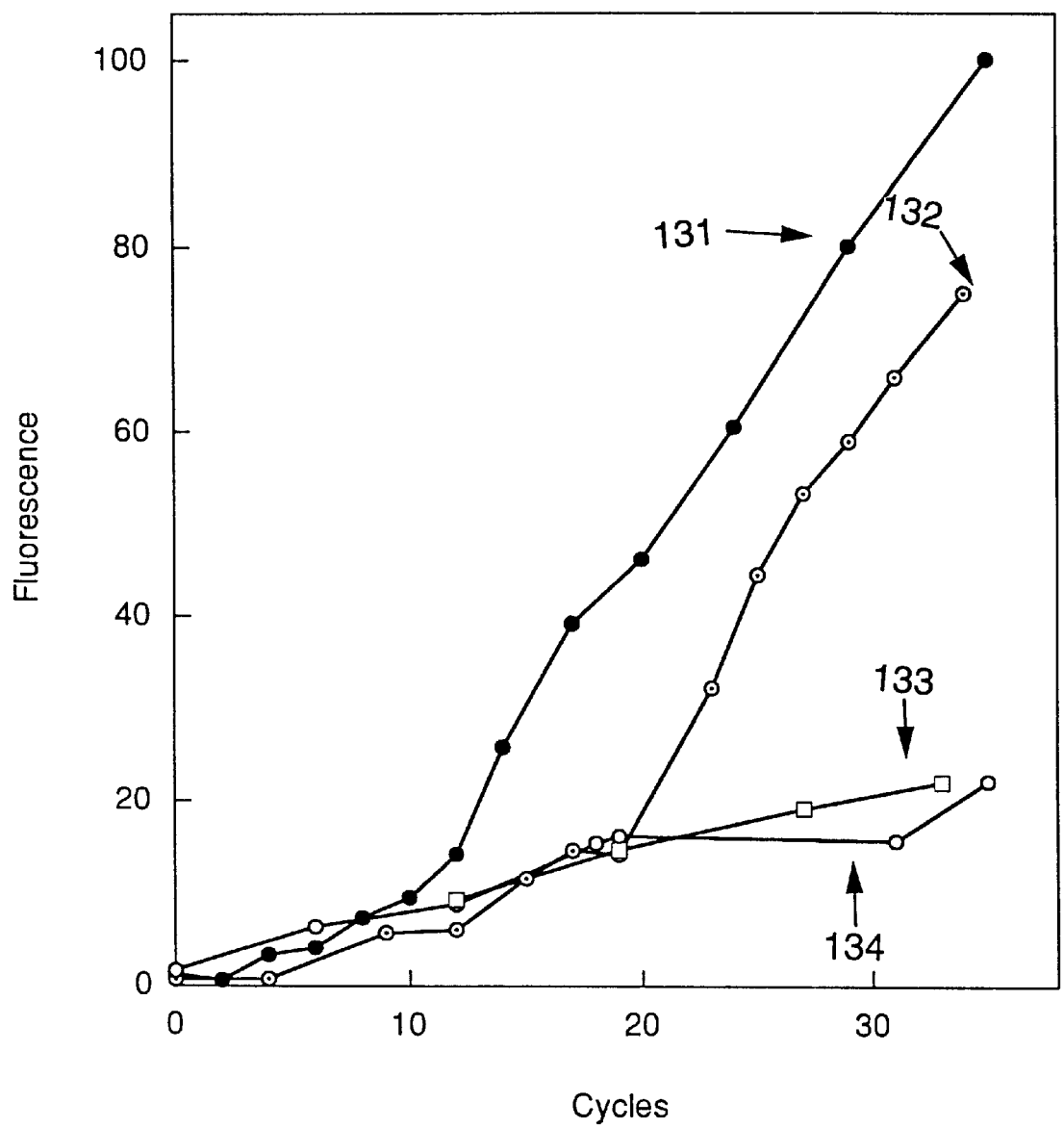
FIG. 13 depicts the progress of a polymerase chain reaction assay using Probe E.

FIG. 13 shows that the progress of a PCR amplification can be monitored and the identity of the amplified product confirmed. Fluorescence at 37° C. increased as the PCR amplification progressed (curves 131 and 132), reporting the accumulation of the expected amplified DNA. The profile of the rise in fluorescence was characterized by an exponential phase in which the amount of amplified DNA was too little to be seen, followed by a linear phase, where the signal became visible. In the first series (curve 131), the exponential phase took about ten cycles to complete. In the second series (curve 132), initiated with a hundred-fold less template, the exponential phase took about seventeen cycles to complete. The linear rises in fluorescence of the two reactions were parallel to each other. The third series (curve 133), in which no DNA was added as template, and the fourth series (curve 134), in which an irrelevant DNA was synthesized, exhibited only small rises in fluorescence. The positive fluorescent signals were easily distinguishable from this background. The observed increase in background fluorescence (FIG. 13) over the course of amplification could be decreased by reducing the amount of polymerase.

Figure 14:
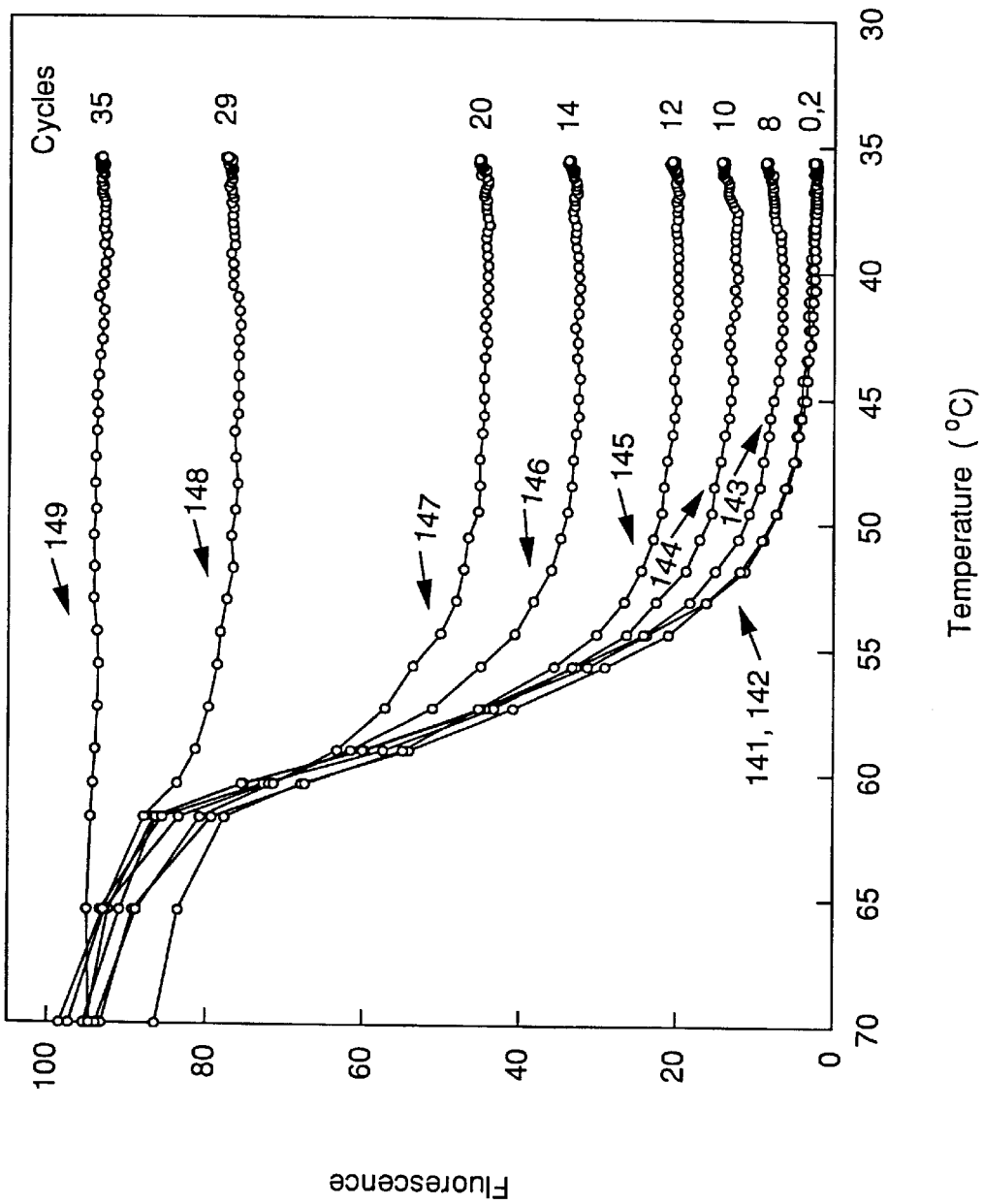
FIG. 14 depicts the level of fluorescence in a polymerase chain reaction as a function of temperature, using Probe E.

To simulate the course of fluorescence within each cycle, the reaction mixtures from the first series were analyzed further. Reactions stopped at various cycles were heated to 95° C. and were allowed to cool to 37° C. The fluorescence of each reaction mixture was measured and plotted as a function of temperature. FIG. 14 shows the results of this experiment.

In the reaction mixtures stopped after zero and two cycles of temperature changes, the fluorescence decreased to a low level as the temperature fell (curves 141 and 142). These curves are virtually indistinguishable. The curves for these reactions are equivalent to the melting profile of Probe E in the absence of target molecules. In the reaction mixture after eight cycles, the fluorescence stabilized at a higher level (curve 143). The level at which the fluorescence stabilized increased progressively as the number of cycles increased (curves 141–149). The change in amplitude of the thermal transition on cooling decreased as more and more PCR product accumulated (curves 141–148) until the 35th cycle, where no thermal transition was apparent (curve 149). By the 35th cycle more PCR product molecules had been made than the number of probe molecules that were added. The family of curves in FIG. 14 also shows that the fluorescence measured at any temperature below about 50° C. is due only to hybridization of Probe E, (which like Probe C, had a Tm of about 61° C.) Detection at temperatures above 50° C., but below the Tm, while proportional to the amount of target, may include fluorescence due to thermal separation of the arms as well as fluorescence due to hybridization.

The PCR reaction products were also quantified using polyacrylamide gel electrophoresis and ethidium bromide staining. A strong correlation was observed between the fluorescence of samples containing Probe E and the fluorescence of samples containing ethidium bromide. The results also demonstrated that the two quantification methods were similar in terms of their sensitivities.

Polyacrylamide gel electrophoresis of the contents of the PCR reactions indicated that there was no detectable degradation of the probes, even after 35 cycles of polymerization.

The probes of this invention with interactive labels may also be used for monitoring other nucleic acid amplification reactions, such as strand displacement amplification reactions and self-sustained sequence replication reactions. Useful probes are designed and used in a manner similar to the probes for polymerase chain reaction products. For isothermal amplifications, fluorescence at any time during the reaction is a direct measure of the amount of nucleic acid synthesized.

EXAMPLE VIII

The superior discriminating power of non-interactively labeled allele-discriminating probes according to this invention has been demonstrated experimentally. Three radioactively labeled probes were compared against a target sequence and a slightly mismatched oligonucleotide to compare the relative discriminating power of the probes.

The first probe, Probe F, was an allele-discriminating probe of this invention. Probe F had a target complement sequence of 15 nucleotides and complementary arms of 5 nucleotides each. The nucleotide sequence of Probe F was identical to the nucleotide sequence of Probe D. Having been tested as a variant with interactive labels, Probe F was thereby shown to be a probe according to this invention under the test conditions for Probe D set forth in Example V. The second probe, Probe G, had the same target complement sequence as Probe D; however, the nucleotides in one of its arms were synthesized in a different order so that its two arms were non-complementary. The third probe, Probe H, had the same target complement sequence as Probe D, but did not have arm sequences. Probes F, G and H possessed a non-interactive label, a radioactive phosphate atom at their 5' ends, rather than an interactive label as in Probe D. The two possible oligonucleotide targets were 19-nucleotides long and were bound to streptavidin-coated paramagnetic particles (Promega) by a biotin group at their 5' end. A target sequence fully complementary to the target complement sequence of Probes F, G and H was located at the 3' end of the first possible target. The second possible target was identical to the first except that the eighth nucleotide from the 3' end was a G, a single internally located mismatch with the target complement sequences of Probes F, G, and H.

Each probe was hybridized to each target under the same conditions reported above for the hybridization of Probe D. The hybrids were captured on the surface of streptavidin-coated paramagnetic particles. The particles were then washed to remove unhybridized probes. After washing, radioactivity bound to the beads was measured with a scintillation counter. By repeating these reactions without targets present, we estimated that the background from probes sticking to the beads was about 6000 counts per minutes.

The first probe gave a reading above background level against the first target (59,000 counts per minute) over five times higher than against the second target (11,000 per minute). The second and third probes gave readings above background against the first target only about 2.5 times higher than against the second target (45,000 to 21,000 and 135,000 to 54,000 counts per minute respectively).

The improved discriminating power of the allele-discriminating probes according to this invention is a surprising discovery. We believe the enhanced discriminatory ability is due to the presence of the nucleic acid affinity pair which allows the probe to assume a conformation which is energetically favored over hybridization to a mismatched sequence, but which is not favored over hybridization to a perfectly complementary target sequence.

These results demonstrate that "allele-discriminating probes" hybridized preferentially to perfectly complementary targets. When an allele-discriminating probe has a non-interactive label, a separation step, such as washing, capture, or other means, can be used to isolate "allele-discriminating probes" hybridized to their targets from probes not so hybridized. Thus, by measuring the signal from the isolated hybrids one can quantitatively or qualitatively determine the presence of the perfectly matched target sequence. Moreover, if an allele-discriminating probe has interactive labels, one need not isolate the hybrids to measure the amount of signal from probes hybridized to perfectly matched targets.

EXAMPLE IX

Tethered Probes

Probes of the present invention with interactive labels may be used in assays wherein they are tethered to a solid support as discussed above and depicted in FIG. 10.

In a preferred embodiment, multiple probes are prepared. Each probe contains a unique target complement sequence. All may contain the same label pair, a fluorophore and a quencher. Each probe also includes an oligonucleotide chain extending from the end of one arm.

Each probe is tethered via an oligonucleotide chain to a specific location on a dipstick assigned to it. This design leaves the target complement sequences free to participate in homogeneous hybridization. In an assay utilizing this embodiment, the dipstick is contacted with a sample that may contain one or several different target sequences.

The tethered probes then interact with their corresponding target sequences. Those probes so interacting will shift to the open state. The dipstick is illuminated with light of an appropriate frequency. Fluorescence from particular locations on the dipstick indicates the presence of corresponding target sequences. Additional configurations of tethered probe assays will be apparent to those skilled in the art.

Tethered probes may be allele-discriminating probes having interactive labels.

REFERENCES

Adachi, A., Gendelman, H. E., Koenig, S., Folks, T., Willey, R., Rabson, A., Martin, M. A., (1986) Production of Acquired Immunodeficiency Syndrome-Associated Retrovirus in Human and Nonhuman Cells Transfected with an Infectious Molecular Clone, Journal of Virology, 59, 284–291.

Cardullo, R. A., Agarwal, S., Flores, C., Zamecnik, P. C. and Wolf, D. E., (1988), Detection of hybridization by non-radiative fluorescence energy transfer, Proc. Natl. Acad. Sci. U.S.A. 85, 8790–8794.

Connoly, B. A. and Rider, P., (1985), Chemical synthesis of oligonucleotide containing a free sulphydryl group and a subsequent attachment of thiol specific probes, Nucleic Acids Res. 13, 4485–4502.

Diamond, S. E., Brewen, J. G., Williams, J. I., Ellwood, M. S., Collins, M. and Fritsch, E. F., (1988), Displacement polynucleotide assay method and polynucleotide complex reagent therefore, U.S. Pat. No. 4,766,062.

Egholm, M., Buchardt, O., Christensen, L., Behrens, C., Freier, S. M., Driver, D. A., Berg, R. H., Kim, S. K. Norden, B., Nielsen, P. E., PNA hybridizes to complementary oligonucleotides obeying the Watson-Crick hydrogen-bonding rules (1993) Nature, 365, 566–568.

Erlich, H. A., Gelfand, D. and Sninsky, J. J., (1991), Recent advances in the polymerase chain reaction, Science 252, 1643–1651.

Freier, S. M., Kierzek, R., Jaeger, J. A., Sugimoto, N., Caruthers, M. H., Neilson, T., Turner, D. H., (1986) Improved free-energy parameters for predictions of RNA duplex stability, Proc. Natl. Acad. Sci. U.S.A., 83, 9373–9377.

Gillespie, D. and Spiegelman, S., (1956), A quantitative assay for DNA-RNA hybrids with DNA immobilized on a membrane, J. Mol. Biol. 12, 829–852.

Guatelli, J. C., Whitfield, K. M., Kwoh, D. Y., Barringer, K. J., Richman, D. D. and Gingeras, T. R., (1990), Isothermal in vitro amplification of nucleic acids by a multienzyme reaction modeled after retroviral replication, Proc. Natl. Acad. Sci. U.S.A. 87, 1874–1878.

Heller, M. J., Morrison, L. E., Prevatt, W. D. and Akin, C., (1983), Homogeneous nucleic acid hybridization diagnostics by nonradiative energy transfer, European Patent Application 070685.

Landegren, U., (1993), Molecular mechanics of nucleic acid sequence amplification, Trends Genet. 9, 199–204.

Lichter, P., Tang, C. J. C., Call, K., Hermanson, G., Evans, G. A., Housman, D. and Ward, D. C., (1990), High resolution mapping of human chromosome 11 by in situ hybridization with cosmid clones, Science 247, 64–69.

Lomeli, H., Tyagi, S., Pritchard, C. G., Lizardi, P. M. and Kramer, F. R., (1989), Quantitative assays based on the use of replicatable hybridization probes, Clin. Chem. 39, 1826–1831.

Matayoshi, E. D., Wang, G. T., Krafft, G. A. and Erickson, J. E., (1990), Novel fluorogenic substrates for assaying retroviral proteases by resonance energy transfer, Science 247, 954–958.

Morrison, L. E., (1987), Competitive homogeneous assays, European Patent Application 87300195.2

Morrison, L. E., (1989), Lifetime-resolved assay procedures, U.S. Pat. No. 4,822,733.

Morrison, L. E., Halder, T. C. and Stols, L. M., (1989), Solution phase detection of polynucleotides using interacting fluorescent labels and competitive hybridization, Analyt. Biochem. 183, 231–244.

Morrison, L. E. and Stols, L. M., (1993), Sensitive fluorescence-based thermodynamic and kinetic measurements of DNA hybridization in solution, Biochemistry 32, 3095–3104.

Muesing, M. A., Smith, D. H., Cabraila, C. D., Benton, C. V., Lasky, L. A. and Eopon, D. J., (1985), Nucleic acid structure and expression of the human AIDS/adenopathy retrovirus, Nature 313, 450–458.

Nelson, P. S., Fry, R. A. and Liu, E., (1989), Bifunctional oligonucleotide probes synthesized using a novel CPG support are able to detect single base pair mutations, Nucleic Acids Res. 17, 7187–7194.

Orum, H., Nielsen, P. E., Egholm, M., Berg, R. H., Buchardt, O. Stanley, C., (1993) Single base pair mutation analysis by PNA directed PCR clamping, Nucleic Acids Res. 21, 5332–5336.

Sambrook, J., Fritsch, E. F. and Maniatis, T., (1989), Molecular cloning—a laboratory manual, Cold Spring Harbor Laboratory Press.

Shore, D., Langowski, J. and Baldwin, R. L., (1981), DNA flexibility studied by covalent closure of short fragments into circles, Proc. Natl. Acad. Sci. U.S.A. 78, 4833–4827.

Tindall, K. R., Kunkel T. A., (1988) Fidelity of DNA Synthesis by the *Thermus aquaticus* DNA Polymerase, Biochem., 27, 6008–6013.

Tinoco, Jun., I., Borer, P., Dengler, B., Levine, M. D., Uhlenbeck, O. C., Crothers, D. M., Gralla, J., (1973), Improved Estimation of Secondary Structure in Ribonucleic Acids, Nature, 246, 40–41.

Uhlmann, E. and Peyman, A., (1988) Antisense oligonucleotides: A New Theraputic Principal, Chemical Reviews 90, 543–584.

Walker, G. T., Fraiser, M. S., Schram, J. L., Little, M. C., Nadeau, J. G. and Malinowski, D. P., (1992), Strand displacement amplification—an isothermal, in vitro DNA amplification technique, Nucleic Acids Res. 20, 1691–1696.

Wang, G. T., Matayoshi, E. D., Huffaker, H. J. and Krafft, G. A., (1991), Design and synthesis of new fluorogenic HIV protease substrates based on resonance energy transfer, Tetrahedron Lett. 31, 6493–6496.

We claim:

1. An oligonucleotide probe that emits a fluorescent signal if contacted with a target sequence under detection conditions of an assay comprising a first arm segment labeled with at least one fluorophore, a second arm segment labeled with at least one quencher, and a target complement sequence complementary to said target sequence, said target complement sequence being intermediate to and joining said first and second arm segments, having a length of not more than 60 nucleotides and forming with said target sequence under said detection conditions a double-stranded hybrid having a first strength;

said first and second arm sequences having sufficient complementarity to one another to form under said detection conditions a double-stranded stem hybrid having a second strength less than said first strength, whereby in the absence of said target sequence fluorescence of said at least one fluorophore is quenched, rendering said probe dark when said at least one fluorophore is stimulated; and said first and second hybrid strengths being selected such that said probe fluoresces when said at least one fluorophore is stimulated under detection conditions in the presence said target sequence.

2. The probe according to claim 1 including a tethering extension to one of said arms.

3. In an assay for detecting at least on nucleic acid target sequence, the improvement comprising generating detectable signal by contacting a sample suspected to contain said at least one target sequence with a probe according to claim 1.

4. The assay according to claim 3 wherein said assay includes an amplification process for creating copies of said at least one target sequence.

5. The assay according to claim 4 wherein said amplification is a polymerase chain reaction.

6. The assay according to claim 4 wherein said probe is added prior to amplification.

7. A kit for performing an assay at least on probe according to claim 1 and instructions for performing said assay.

8. The kit of reagents according to claim 7, further comprising amplification reagents capable of creating copies of said at least one target sequence.

9. The kit of reagents according to claim 8 wherein said amplification reagents are polymerase chain reaction reagents.

10. A multiplex assay for at least two different nucleic acid target sequences comprising the steps of adding to a sample suspected to contain one or more of said target sequences a probe according to claim 1 that is specific for each one of said target sequences to the exclusion of the others of said target sequences, wherein the fluorescent signal emitted by each probe is detectably different from the fluorescent signal emitted by every other probe; stimulating the fluorophores of said probes; and detecting fluorescence emissions from said probes.

11. The assay according to claim 10 wherein said assay includes an amplification process for creating copies of said at least two different nucleic acid target sequences.

12. The assay according to claim 11 wherein said amplification is a polymerase chain reaction.

* * * * *